(12) United States Patent
Zheng et al.

(10) Patent No.: US 11,248,088 B2
(45) Date of Patent: Feb. 15, 2022

(54) METHOD TO MAKE FLUORESCENT NANODOTS FOR FAST BACTERIA STAINING AND BROAD SPECTRUM ANTIMICROBIAL APPLICATIONS

(71) Applicant: Agency for Science, Technology and Research, Singapore (SG)

(72) Inventors: Xin Ting Zheng, Singapore (SG); Yen Nee Tan, Singapore (SG); Victor Hesheng Xu, Singapore (SG)

(73) Assignee: AGENCY FOR SCIENCE, TECHNOLOGY AND RESEARCH, Singapore (SG)

(*) Notice: Subject to any disclaimer, the term of this patent is extended or adjusted under 35 U.S.C. 154(b) by 94 days.

(21) Appl. No.: 16/166,017

(22) Filed: Oct. 19, 2018

(65) Prior Publication Data
US 2019/0161579 A1  May 30, 2019

(30) Foreign Application Priority Data
Oct. 19, 2017  (SG) ............................. 10201708588Y

(51) Int. Cl.
| | | |
|---|---|---|
| *A01N 37/44* | (2006.01) | |
| *A61K 31/787* | (2006.01) | |
| *A61K 9/51* | (2006.01) | |
| *B82Y 15/00* | (2011.01) | |
| *B82Y 40/00* | (2011.01) | |
| *C08G 73/02* | (2006.01) | |
| *G01N 1/30* | (2006.01) | |
| *B82Y 5/00* | (2011.01) | |
| *C08L 101/00* | (2006.01) | |
| *A01N 37/50* | (2006.01) | |
| *A61K 9/14* | (2006.01) | |
| *B82Y 30/00* | (2011.01) | |

(52) U.S. Cl.
CPC ............ *C08G 73/02* (2013.01); *A01N 37/44* (2013.01); *A01N 37/50* (2013.01); *A61K 9/51* (2013.01); *A61K 31/787* (2013.01); *B82Y 5/00* (2013.01); *B82Y 15/00* (2013.01); *B82Y 40/00* (2013.01); *C08L 101/00* (2013.01); *G01N 1/30* (2013.01); *A61K 9/145* (2013.01); *B82Y 30/00* (2013.01); *G01N 2001/302* (2013.01)

(58) Field of Classification Search
CPC ......... G01N 1/30; C08L 101/00; B82Y 40/00; B82Y 15/00; B82Y 5/00; A61K 31/787; A61K 9/51; A01N 37/44; A01N 37/50; C08G 73/02
See application file for complete search history.

(56) References Cited

FOREIGN PATENT DOCUMENTS

| CN | 105776179 A | 7/2016 |
|---|---|---|
| CN | 106744809 A | 5/2017 |

OTHER PUBLICATIONS

Yang (Chemical Communication, Issue 48, pp. 380-382, Published 2012) (Year: 2012).*
Xu (Chemistry A European Journal, pp. 2276-2283, Published 2013) (Year: 2013).*
Sachdev (Royal Society of Chemistry Advnaces, Issue 4, pp. 20915-20921, Published 2014) (Year: 2014).*
Du et al. (Royal Society of Chemistry Advances, Published 2014, pp. 37563-37541) (Year: 2014).*
ASTM International "ASTM D4001-13, Standard Test Method for Determination of Weight-Average Molecular Weight of Polymers by Light Scattering" 2013, available online at <https://www.astm.org/Standards/D4001.htm>.
Debye "Molecular weight determination by light scattering" The Journal of Physical and Colloid Chemistry, vol. 51, No. 1, Jan. 1, 1947, pp. 18-32.
Defez et al. "Risk factors for multidrug resistant Pseudomonas aeruginosa nosocomial infection" Journal of Hospital Infection, vol. 57, No. 3, Jul. 1, 2004, pp. 209-216.
Freedonia "Disinfectant & Antimicrobial Chemicals to 2017— Demand and Sales Forecasts, Market Share, Market Size, Market Leaders" Jun. 2013, available online at <https://www.freedoniagroup.com/disinfectant-antimicrobial-chemicals.html>.
Gong et al. "Phosphorus and nitrogen dual-doped hollow carbon dot as a nanocarrier for doxorubicin delivery and biological imaging" ACS Applied Materials & Interfaces, vol. 8, No. 18, Apr. 18, 2016 pp. 11288-11297.
Grohs et al. "In vitro bactericidal activities of linezolid in combination with vancomycin, gentamicin, ciprofloxacin, fusidic acid, and rifampin against *Staphylococcus aureus*" Antimicrobial Agents and Chemotherapy, vol. 47, No. 1, Jan. 2003, pp. 418-420.
Hancock et al. "The role of antimicrobial peptides in animal defenses" Proceedings of the National Academy of Sciences, vol. 97, No. 16, Aug. 1, 2000, pp. 8856-8861.
He et al. "Effects of particle size and surface charge on cellular uptake and biodistribution of polymeric nanoparticles" Biomaterials, vol. 31, No. 13, Feb. 6, 2010, pp. 3657-3666.

(Continued)

*Primary Examiner* — Alma Pipic
(74) *Attorney, Agent, or Firm* — Womble Bond Dickinson (US) LLP

(57) ABSTRACT

The present invention relates to a hybrid nanodot made by a process comprising a step of reacting a mixture of an amino acid and a polymer selected from polycationic polymers or any copolymers or derivatives of these polymers under hydrothermal reaction conditions. The present invention also relates to a process for synthesizing said hybrid nanodots.

17 Claims, 15 Drawing Sheets

(56) References Cited

OTHER PUBLICATIONS

Holt et al. "Interaction of silver (I) ions with the respiratory chain of *Escherichia coli*: an electrochemical and scanning electrochemical microscopy study of the antimicrobial mechanism of micromolar Ag+" Biochemistry, vol. 44, No. 39, Sep. 2, 2005, pp. 13214-13223.
Hu et al. "Engineering carbon materials from the hydrothermal carbonization process of biomass" Advanced Materials, vol. 22, Issue 7, Feb. 12, 2010, pp. 813-828.
Janssen et al. "Improved culturability of soil bacteria and isolation in pure culture of novel members of the divisions Acidobacteria, Actinobacteria, Proteobacteria, and Verrucomicrobia" Applied and Environmental Microbiology, vol. 68, No. 5, May 1, 2002, pp. 2391-2396.
Kittler et al. "Toxicity of silver nanoparticles increases during storage because of slow dissolution under release of silver ions" Chemistry of Materials, vol. 22, No. 16, Jul. 30, 2010, pp. 4548-4554.
Nadkami et al. "Determination of bacterial load by real-time PCR using a broad-range (universal) probe and primers set" Microbiology, vol. 148, No. 1, Jan. 1, 2002, pp. 257-266.
Nikaido "Multidrug resistance in bacteria" Annual Review of Biochemistry, vol. 78, Feb. 20, 2009, pp. 119-146.
Nugent et al. "Reliability of diagnosing bacterial vaginosis is improved by a standardized method of gram stain interpretation" Journal of Clinical Microbiology, vol. 29, No. 2, Jan. 31, 1991, pp. 297-301.
Obritsch et al. "Nosocomial infections due to multidrug resistant Pseudomonas aeruginosa: epidemiology and treatment options" Pharmacotherapy: The Journal of Human Pharmacology and Drug Therapy, vol. 25, No. 10, Sep. 30, 2005, pp. 1353-1364.
Penna et al. "Paracetamol poisoning in children and hepatotoxicity" British Journal of Clinical Pharmacology, vol. 32, No. 2, Jul. 31, 1991, pp. 143-149.
Pranantyo et al. "Conjugation of polyphosphoester and antimicrobial peptide for enhanced bactericidal activity and biocompatibility" Biomacromolecules, vol. 17, No. 12, Nov. 9, 2016, pp. 4037-4044.
Rapireddy et al. "RTD-1Mimic containing γPNA scaffold exhibits broad-spectrum antibacterial activities" Journal of the American Chemical Society, vol. 134, No. 9, Feb. 14, 2012, pp. 4041-4044.
Salatin et al. "Effect of the surface modification, size, and shape on cellular uptake of nanoparticles" Cell Biology International, vol. 39, Issue 8, Mar. 19, 2015, pp. 881-890.
Strom et al. "Antimicrobial activity of short arginine and tryptophan rich peptides" Journal of Peptide Science, vol. 8, No. 8, Jul. 22, 2002 pp. 431-437.
Titirici et al. "Chemistry and materials options of sustainable carbon materials made by hydrothermal carbonization" Chemical Society Reviews, vol. 39, No. 1, Sep. 24, 2009, pp. 103-116.
Tossi et al. "Amphipathic, a-helical antimicrobial peptides" Peptide Science, vol. 55, No. 1, Jan. 12, 2004, pp. 4-30.
Wu et al. "Interaction of the cyclic antimicrobial cationic peptide bactenecin with the outer and cytoplasmic membrane" Journal of Biological Chemistry, vol. 274, No. 1, Jan. 1, 1999, pp. 29-35.
Xu et al. "Critical review of desalination concentrate management, treatment and beneficial use" Environmental Engineering Science, vol. 30, No. 8, Aug. 14, 2013, pp. 502-514.
Yang et al. "Long hydrophilic-and-cationic polymers: a different pathway toward preferential activity against bacterial over mammalian membranes" Biomacromolecules, vol. 15, No. 9, Jul. 28, 2014, pp. 3267-3277.
Zheng et al. "Self-targeting fluorescent carbon dots for diagnosis of brain cancer cells" ACS Nano, vol. 9, No. 11, Oct. 12, 2015, pp. 11455-11461.
Zhong et al. "Short synthetic B-sheet antimicrobial peptides for the treatment of multidrug resistant pseudomonas aeruginosa burn wound infections" Advanced Healthcare Materials, vol. 6, Issue 7, Jan. 30, 2017, pp. 1-9.
Zou et al. "Design and synthesis of amphiphilic xanthone-based, membrane-targeting antimicrobials with improved membrane selectivity" Journal of Medicinal Chemistry, vol. 56, No. 6, Feb. 26, 2013, pp. 2359-2373.
The Search Report and Written Opinion of counterpart Singaporean Application No. 10201809275W dated Jun. 16, 2021, 10 pages.
Zeng et al., "N, S co-doped carbon dots with orange luminescence synthesized through polymerization and carbonization reaction of amino acids", Elsevier, Mar. 14, 2015, 8 pages.
Choi et al., "Microwave-assisted synthesis of luminescent and biocompatible lysine-based carbon quantum dots", Elsevier, Dec. 9, 2016, 7 pages.
Dou et al., "Multi-functional fluorescent carbon dots with antibacterial and gene delivery properties", RSC Advances, May 13, 2015, 6 pages.
Sachdev et al., "Implications of surface passivation on physicochemical and bioimaging properties of carbon dots", RSC Advances, Apr. 25, 2014, 7 pages.

\* cited by examiner

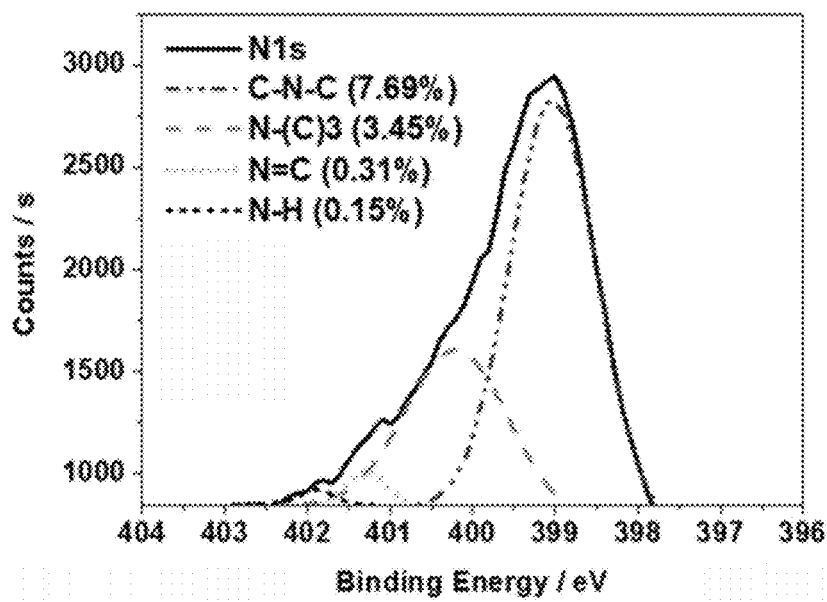
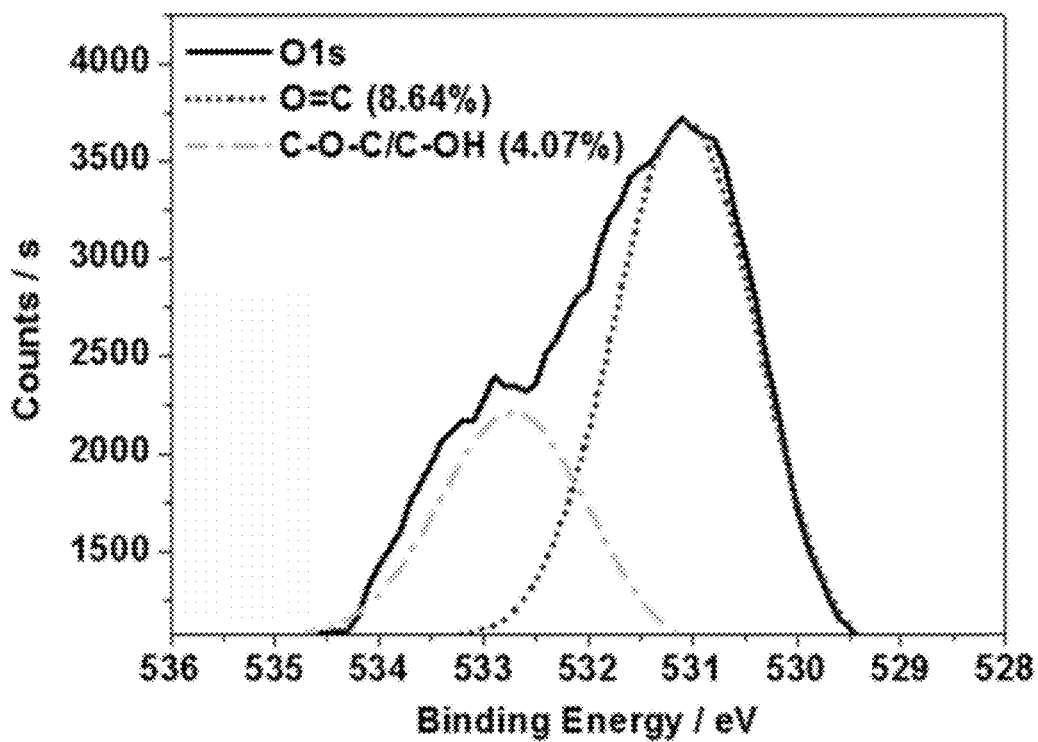

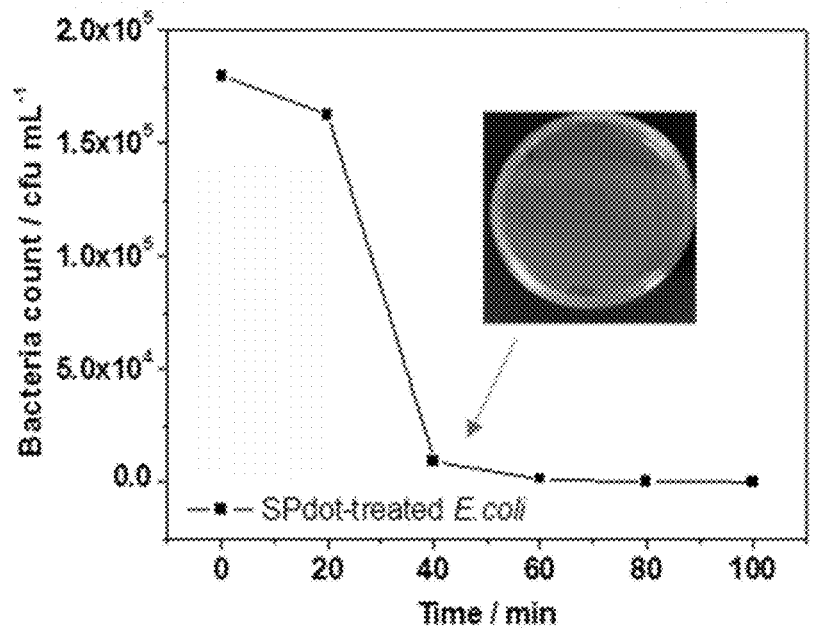
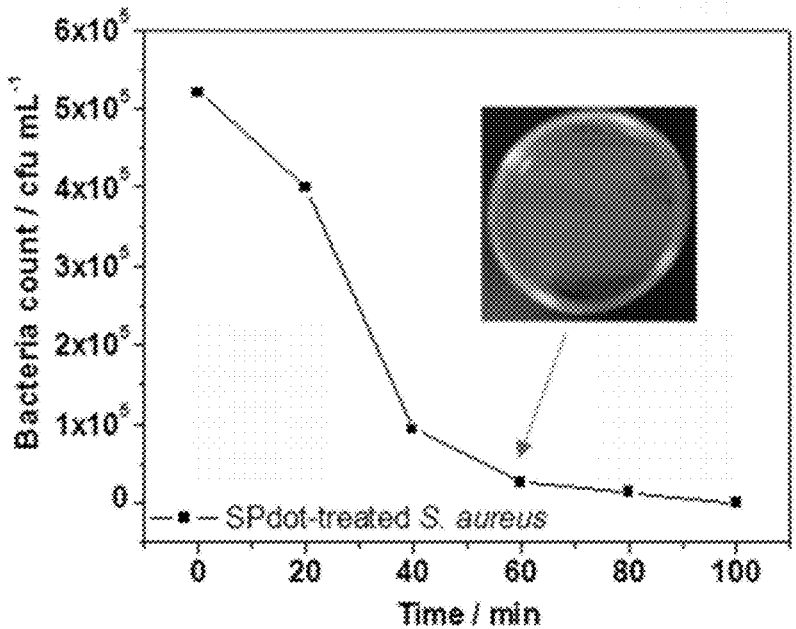

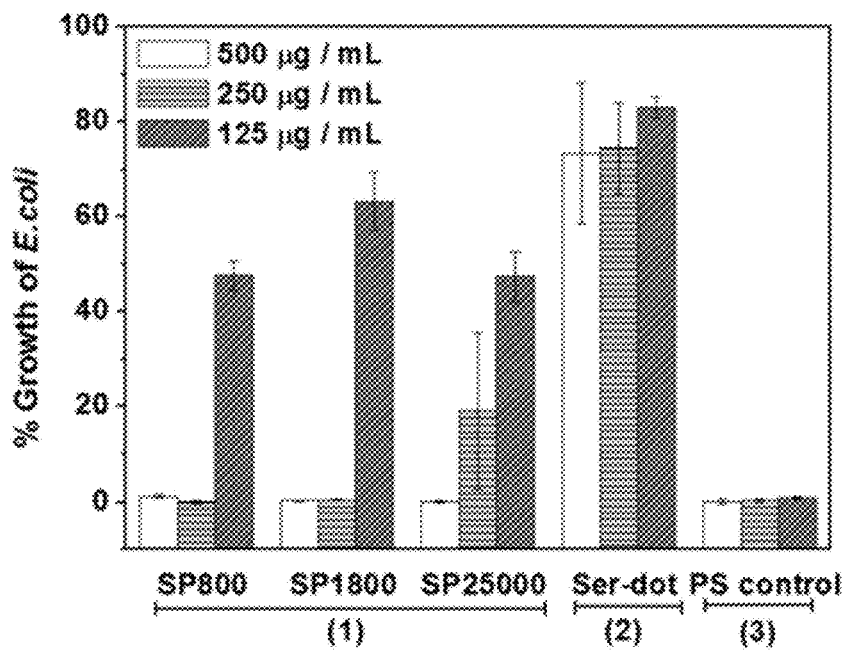
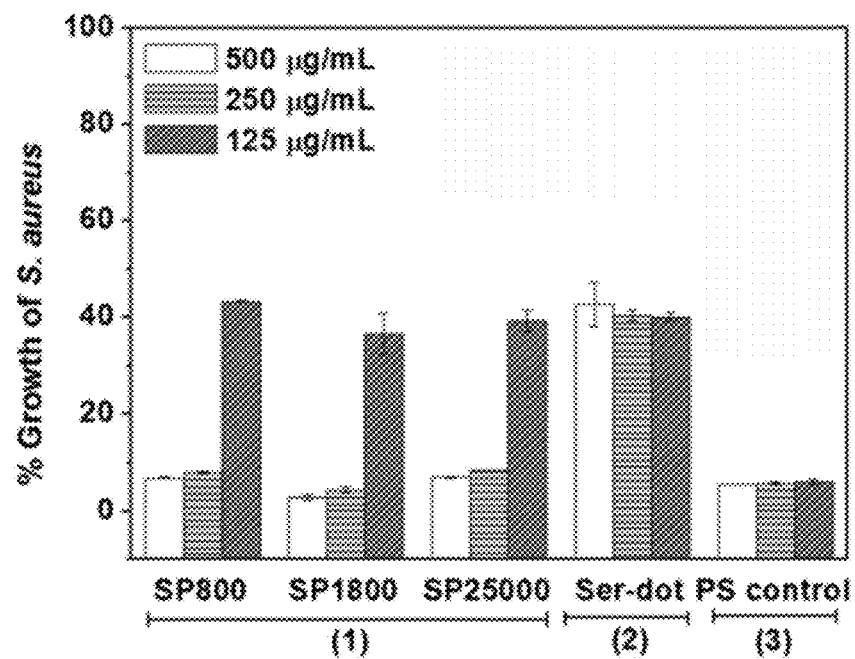

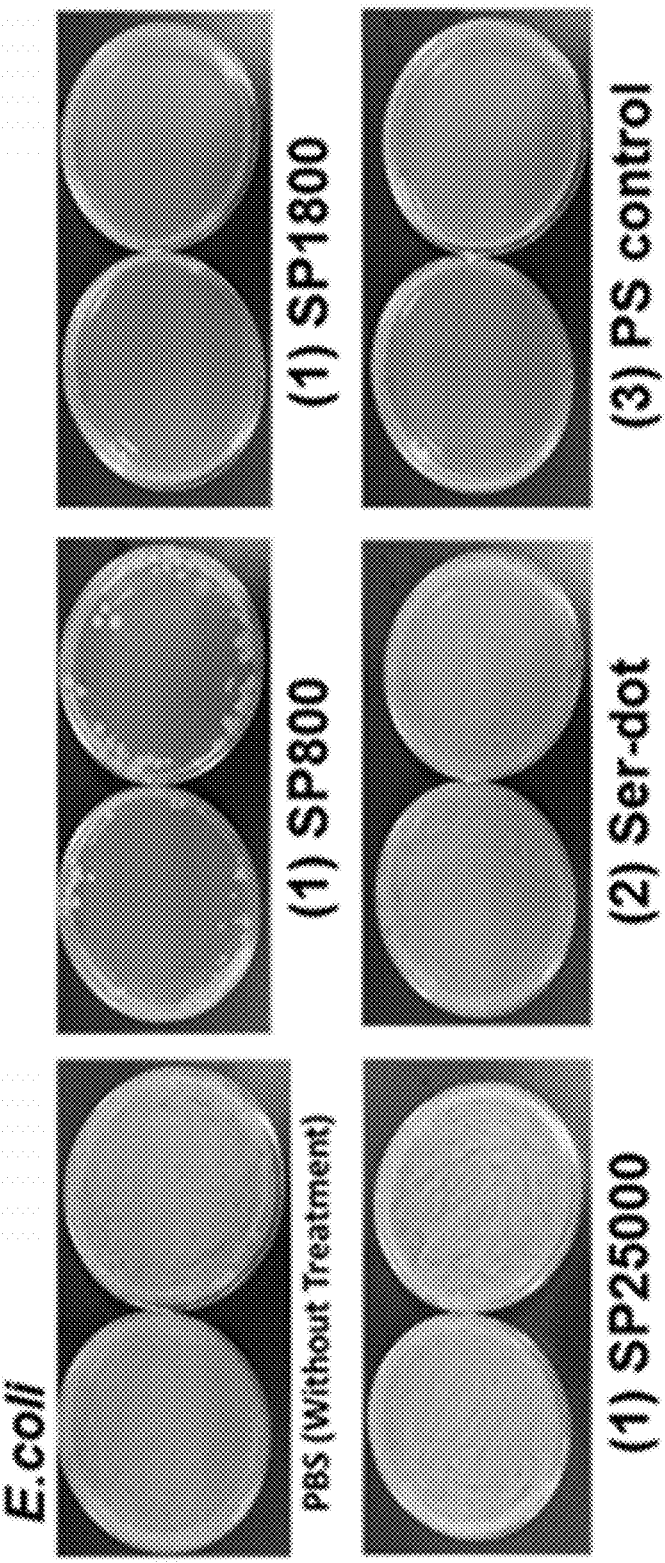

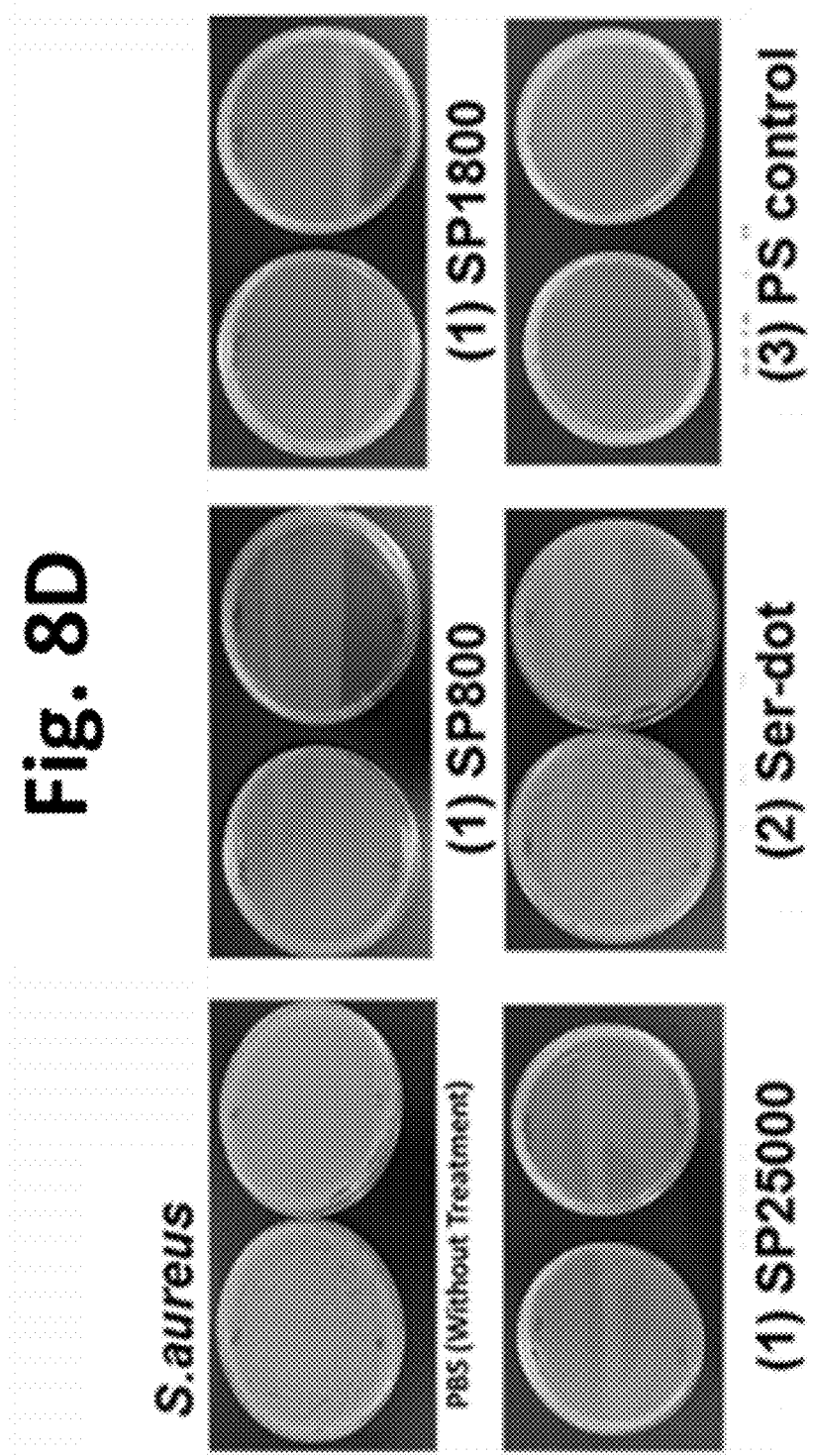

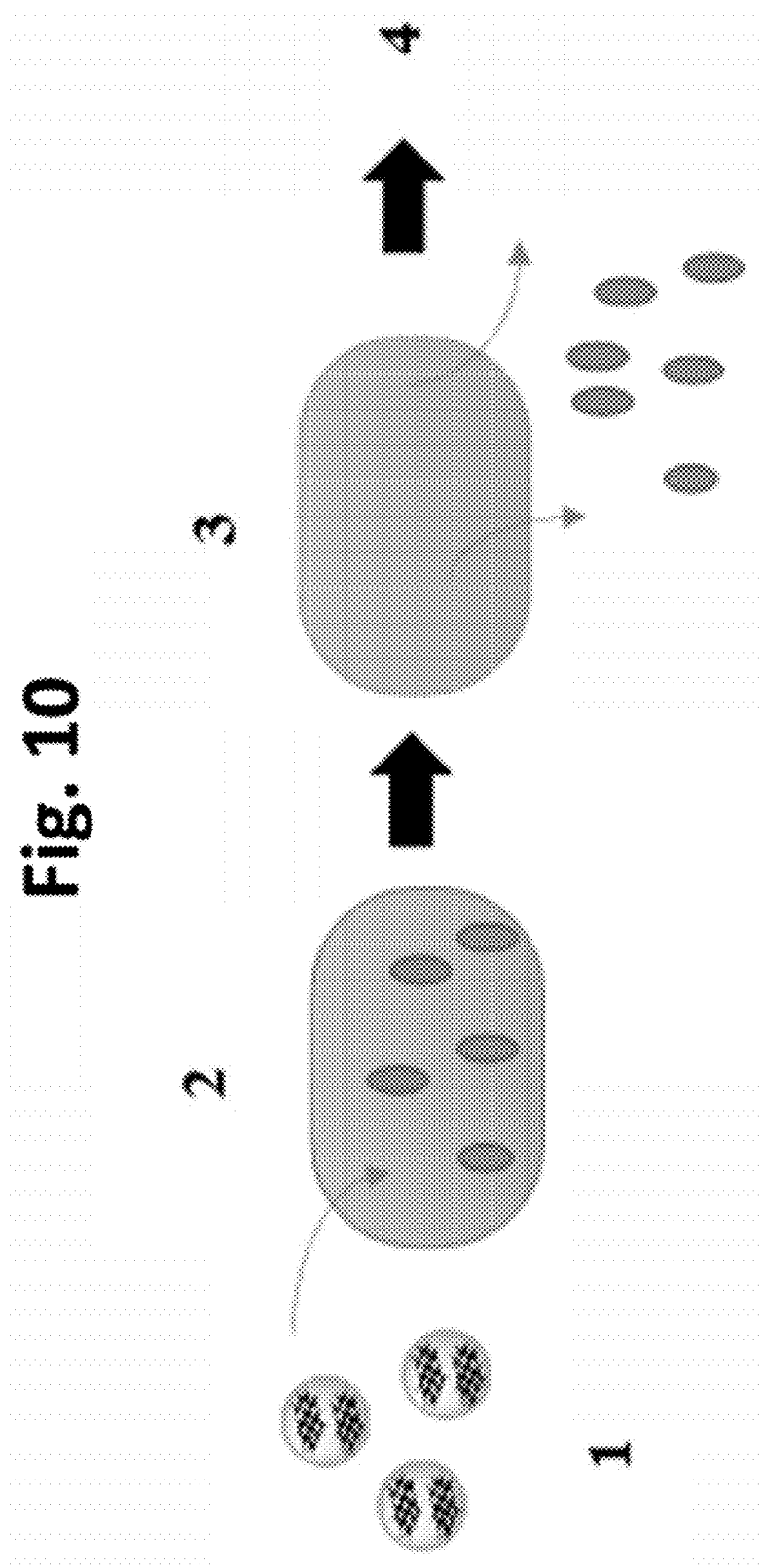

METHOD TO MAKE FLUORESCENT NANODOTS FOR FAST BACTERIA STAINING AND BROAD SPECTRUM ANTIMICROBIAL APPLICATIONS

TECHNICAL FIELD

The present invention generally relates to an amino acid-polymer hybrid nanodots and processes for synthesizing said hybrid nanodots. The present invention also relates to hybrid nanodots for fluorescence-based imaging and/or for combating bacteria.

BACKGROUND ART

The emergence of microbial resistance to conventional antibiotics in recent decades is a serious challenge and has led to an overwhelming demand for new antimicrobial agents. In 2013, the market value in the United States of America for antimicrobial agents reached $1.2 billion per annum, and was forecasted to rise 6.1% annually to $1.6 billion in 2017. In practice, commonly used antibacterial agents (for example, ozone, and hypochlorite) tend to cause contamination or salting of freshwater sources. Silver is also known to be an emerging antimicrobial agent due to the ability of the silver ion ($Ag^+$) to disrupt essential biochemical pathways in both bacteria and human cells. Although $Ag^+$ is extremely potent against bacteria, its high toxicity can pose significant problems to human health and well-being when used excessively. Antimicrobial peptides and cationic polymers are also popular solutions to combat bacteria, but many of them possess high toxicity towards mammalian cells.

Widespread bacterial infection has also made fast diagnosis vital for clinical treatments. Extensive efforts have also been devoted to developing new methods for bacterial detection. Conventional detection methods include Gram staining, plate counting, and polymerase chain reaction (PCR). Despite their success in many aspects, these technologies still have limitations such as low reproducibility, laborious procedures, long operation time and proneness to false positive results.

Therefore, there is a need to provide an antimicrobial agent and a bacterial detection method that overcome, or at least ameliorate, one or more of the disadvantages described above.

In particular, there is a need to provide a metal-free antimicrobial agent with potent antimicrobial activity and mammalian cell compatibility.

Additionally, there is also a need to provide fast bacterial detection methods without sophisticated preparation and instrumentation.

SUMMARY

In one aspect of the present disclosure, there is provided a hybrid nanodot made by a process comprising a step of reacting a mixture of an amino acid and a polymer selected from polycationic polymers or any copolymers or derivatives of these polymers under hydrothermal reaction conditions.

Advantageously, the hybrid nanodots of the present disclosure may possess tunable photoluminescent, antimicrobial and bacteria-staining properties. Further advantageously, the hybrid nanodots of the present disclosure may be able to disrupt bacterial membrane, release intracellular proteins, thus allowing for potent antibacterial effects. The antibacterial effects of the hybrid nanodots of the present disclosure may be towards broad-spectrum bacteria (both gram-positive and gram-negative) and they may be advantageously effective against multidrug-resistant superbugs, such as *Pseudomonas aeruginosa*.

Also advantageously, the hybrid nanodots of the present disclosure may have small sizes and spherical shapes which may lead to fast interaction between the hybrid nandot and bacteria, which may thus achieve bacterial inhibition almost instantaneously.

Further advantageously, the hybrid nanodots of the present disclosure may have excitation-dependent fluorescent properties which may allow for simultaneous staining of bacteria.

Also advantageously, the hybrid nanodot as defined herein may possess many unique properties such as small size, near neutral charge, bright fluorescence, and abundant functional groups.

Further advantageously, the abundant functional groups on the surface of said hybrid nanodot may be facile for conjugation with biomolecules such as aptamers or antibodies for selective detection of a particular bacteria of interest.

In another aspect of the present disclosure, there is provided a process for producing a hybrid nanoparticle as defined herein, comprising the process steps of:
  (a) dissolving the amino acid and polycationic polymer in an aqueous medium;
  (b) heating the obtained solution at elevated temperature and increased pressure; and
  (c) separating the hybrid nanoparticles that have formed from the reaction mixture.

Advantageously, the synthesis process defined herein may be a simple scalable one-step hydrothermal reaction from amino acids and selected polymers. Hence, advantageously, said synthesis process may be scaled-up in a straightforward approach.

Also advantageously, the formulation (amino acid-to-polymer ratio) of the hybrid nanodot as defined herein may be finely tuned to control the surface properties, such as zeta potential to be near neutral. Therefore, advantageously, said hybrid nanodot may preferentially disrupt membranes of bacteria cells but not mammalian cells, and thus lead to potent antimicrobial activity while improving mammalian cell biocompatibility to achieve a satisfactory therapeutic index.

In yet another aspect of the present disclosure, there is provided a hybrid particle as defined herein, obtained by any of the processes as defined herein.

In a further aspect of the present disclosure, there is provided a hybrid nanodot as defined herein for fluorescence-based imaging of cells, preferably bacteria.

Advantageously, the hybrid nanodot as defined herein may possess excitation-dependent fluorescence with high quantum yield. Further advantageously, said hybrid nanodot may possess small size and spherical shape and can undergo fast interaction with the bacteria. When used, said hybrid nanodot may undergo efficient uptake by the bacteria into intracellular compartments, and may be an efficient staining agent for potential bacterial detection applications. Therefore, advantageously, said hybrid nanodot has high potential for simultaneous multicolor bacteria imaging and detection.

In another aspect of the present disclosure, there is provided a hybrid nanodot as defined herein for combating bacteria.

Advantageously, the hybrid nanodot as defined herein may possess small size and spherical shape and can undergo fast interaction with the bacteria membranes. When used, said hybrid nanodot may demonstrate strong bacteria membrane disruption capability.

Advantageously, said hybrid nanodot may effectively inhibit a broad spectrum of bacteria growth (both gram-positive and gram-negative). Further advantageously, the inhibition may occur immediately upon simple mixing. When used, said hybrid nanodot may be able to kill more than 99% of bacteria species within 60 minutes.

Advantageously, the hybrid nanodot as defined herein may also be effective against multidrug-resistant bacteria.

In yet another aspect of the present disclosure, there is provided an antimicrobial composition comprising a hybrid nanodot as defined herein, optionally together with customary solvents, additives or fillers.

In a further aspect of the present disclosure, there is provided a use of the antimicrobial composition as defined herein to combat gram-positive and/or gram-negative bacteria in hygiene applications, preferably surface disinfection.

In another aspect of the present disclosure, there is provided a method of combating bacteria by exposing the bacteria with a hybrid nanodot as defined herein.

Advantageously, said method of combating bacteria by exposing the bacteria with the hybrid nanodot may involve interactions of said hybrid nanodot with the bacteria and physically damaging/disrupting the bacterial cell membrane, leading to substantial release of intracellular proteins without destroying the overall bacterial morphology. Hence advantageously, the nature of said antibacterial mechanism may render the bacteria less likely to develop resistance. Thus, advantageously, said hybrid nanodot has high potential to be used as a potent antimicrobial agent.

Definitions

The following words and terms used herein shall have the meaning indicated:

The term "hybrid nanodot" refers to a nanometer-scale (e.g., not more than 100 nm) localized structure or particle made from two or more constituent materials with significantly different physical or chemical properties. The hybrid nanodot of the invention may be defined as a nitrogen-doped carbon nanodot, but is not limited thereto.

The term "hydrothermal reaction" refers to a technique of producing structures from high-temperature aqueous solutions at high vapor pressures.

The term "combating bacteria" refers to the inhibition of growth or multiplication as well as the killing of bacteria.

As used herein, all ratios refer to weight ratios unless otherwise stated.

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means+/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and sub-generic groupings falling within the generic disclosure also form part of the disclosure. This includes the generic description of the embodiments with a proviso or negative limitation removing any subject matter from the genus, regardless of whether or not the excised material is specifically recited herein.

DETAILED DESCRIPTION OF EMBODIMENTS

Exemplary, non-limiting embodiments of the present invention will now be disclosed.

The hybrid nanodot defined in the disclosure may be synthesized by dissolving an amino acid and a polymer in an aqueous medium. The obtained solution may then be heated at elevated temperature and increased pressure. The produced hybrid nanodots may then be separated from the reaction mixture.

The inventors have found that the newly synthesized hybrid nanodots can be used to stain bacteria for imaging and sensing purposes and possess antimicrobial properties against gram-positive and gram negative bacteria, as well as multidrug-resistant bacteria such as *P. aeruginosa*. Advantageously, the hybrid nanodots can be obtained in a simple scalable one-step hydrothermal reaction from amino acids and selected polymers.

The hybrid nanodot may be made by a process comprising a step of reacting a mixture of an amino acid and a polymer selected from polycationic polymers or any copolymers or derivatives of these polymers under hydrothermal reaction conditions.

The hybrid nanodot may be metal free. This is advantageous as metal-containing agents may be toxic which can pose significant problems to human health and well-being when used excessively.

The hybrid nanodot may have a surface zeta potential near neutral. This is advantageous as the hybrid nanodots may be biocompatible to mammalian cells, leading to a high therapeutic index.

The amino acid may contain a polar side chain. The amino acid may be serine, threonine, cysteine, tyrosine, asparagine, glutamine, arginine, histidine, lysine, aspartic acid, glutamic acid or mixtures thereof. The amino acid may be serine.

The polymer may be selected from polycationic polymers or any copolymers or derivatives of these polymers. The polycationic polymer may be poly(ethylene imine), poly-L-lysine, or chitosan. The polycationic polymer may be branched poly(ethylene imine).

The average molecular weight of the polycationic polymer may be about 200 to 50,000 g/mol, about 2,200 to 50,000 g/mol, about 4,200 to 50,000 g/mol, about 6,200 to 50,000 g/mol, about 8,200 to 50,000 g/mol, about 10,200 to 50,000 g/mol, about 12,200 to 50,000 g/mol, about 14,200 to 50,000 g/mol, about 16,200 to 50,000 g/mol, about 18,200 to 50,000 g/mol, about 20,200 to 50,000 g/mol, about 22,200 to 50,000 g/mol, about 24,200 to 50,000 g/mol, about 26,200 to 50,000 g/mol, about 28,200 to 50,000 g/mol, about 30,200 to 50,000 g/mol, about 32,200 to 50,000 g/mol, about 34,200 to 50,000 g/mol, about 36,200 to 50,000 g/mol, about 38,200 to 50,000 g/mol, about 40,200 to 50,000 g/mol, about 42,200 to 50,000 g/mol, about 44,200 to 50,000 g/mol, about 46,200 to 50,000 g/mol, about 48,200 to 50,000 g/mol, about 200 to 48,000 g/mol, about 200 to 46,000 g/mol, about 200 to 44,000 g/mol, about 200 to 42,000 g/mol, about 200 to 40,000 g/mol, about 200 to 38,000 g/mol, about 200 to 36,000 g/mol, about 200 to 34,000 g/mol, about 200 to 32,000 g/mol, about 200 to 30,000 g/mol, about 200 to 28,000 g/mol, about 200 to 26,000 g/mol, about 200 to 24,000 g/mol, about 200 to 22,000 g/mol, about 200 to 20,000 g/mol, about 200 to 18,000 g/mol, about 200 to 16,000 g/mol, about 200 to 14,000 g/mol, about 200 to 12,000 g/mol, about 200 to 10,000 g/mol, about 200 to 8,000 g/mol, about 200 to 6,000 g/mol, about 200 to 4,000 g/mol, about 200 to 2,000 g/mol, or about 200 g/mol, about 500 g/mol, about 1000 g/mol, about 1500 g/mol, about 2000 g/mol, about 2500 g/mol, about 3000 g/mol, about 3500 g/mol, about 4000 g/mol, about 4500 g/mol, about 5000 g/mol, about 5500 g/mol, about 6000 g/mol, about 6500 g/mol, about 7000 g/mol, about 7500 g/mol, about 8000 g/mol, about 8500 g/mol, about 9000 g/mol, about 9500 g/mol, about 10,000 g/mol, about 10,500 g/mol, about 11,000 g/mol, about 11,500 g/mol, about 12,000 g/mol, about 12,500 g/mol, about 13,000 g/mol, about 13,500 g/mol, about 14,000 g/mol, about 14,500 g/mol, about 15,000 g/mol, about 15,500 g/mol, about 16,000 g/mol, about 16,500 g/mol, about 17,000 g/mol, about 17,500 g/mol, about 18,000 g/mol, about 18,500 g/mol, about 19,000 g/mol, about 19,500 g/mol, about 20,000 g/mol, about 25,000 g/mol, about 30,000 g/mol, about 35,000 g/mol, about 40,000 g/mol, about 45,000 g/mol, about 50,000 g/mol, or any range or value therein. The average molecular weight of the polycationic polymer may be about 1,000 to 5,000 g/mol, or about 1,000 g/mol, about 2,000 g/mol, about 3,000 g/mol, about 4,000 g/mol, about 5,000 g/mol, or any value or range therein. The average molecular weight of the polycationic polymer may be about 1,500 to 2,100 g/mol, or about 1,500 g/mol, about 1,600 g/mol, about 1,700 g/mol, about 1,800 g/mol, about 1,900 g/mol, about 2,000 g/mol, about 2,100 g/mol, or any value or range therein.

The weight ratio of amino acid to polycationic polymer may be about 10:1 to 1:2. The weight ratio of amino acid to polycationic polymer may be about 10:1 to 1:2, or about about 9.75:1, about 9.5:1, about 9.25:1, about 9:1, about 8.75:1, about 8.5:1, about 8.25:1, about 8:1, about 7.75:1, about 7.5:1, about 7.25:1, 7:1, about 6.75:1, about 6.5:1, about 6.25:1, about 6:1, about 5.75:1, about 5.5:1, about 5.25:1, about 5:1, about 4.75:1, about 4.5:1, about 4.25:1, about 4:1, about 3.75:1, about 3.5:1, about 3.25:1, about 3:1, about 2.75:1, about 2.5:1, about 2.25:1, about 2:1, about 1.75:1, about 1.5:1, about 1.25:1, about 1:1, about 0.75:1, about 0.5:1 (1:2), or any range or value therein. The weight ratio of amino acid to polycationic polymer may be 5:1 to 1:1, or about 5:1, about 4.75:1, about 4.5:1, about 4.25:1, about 4:1, about 3.75:1, about 3.5:1, about 3.25:1, about 3:1, about 2.75:1, about 2.5:1, about 2.25:1, about 2:1, about 1.75:1, about 1.5:1, about 1.25:1, about 1:1, or any value or range therein. The weight ratio of amino acid to polycationic polymer may be about 3:1 to 1.25:1, or about 3:1, about 2.75:1, about 2.5:1, about 2.25:1, about 2:1, 1.75:1, about 1.5:1, about 1.25:1, or any value or range therein. The weight ratio of amino acid to polycationic polymer may be about 2.5:1 to 1.5:1, or about 2.25:1, about 2:1, about 1.75:1, about 1.5:1, or any value or range therein.

The mixing ratio of amino acid and polycationic polymer may also be chosen in a way that the zeta potential of the hybrid nanodot surface is near neutral. This is advantageous as this means that the hybrid nanodots of the present disclosure may be tuned or adjusted according to needs.

The hybrid nanodot may have a particle size of about 1 to 100 nm, about 10 to 100 nm, about 20 to 100 nm, about 30 to 100 nm, about 40 to 100 nm, about 50 to 100 nm, about 60 to 100 nm, about 70 to 100 nm, about 80 to 100 nm, about 90 to 100 nm, about 1 to 90 nm, about 1 to 80 nm, about 1 to 70 nm, about 1 to 60 nm, about 1 to 50 nm, about 1 to 40 nm, about 1 to 30 nm, about 1 to 20 nm, about 1 to 10 nm, or about 1 nm, about 5 nm, about 10 nm, about 15 nm, about 20 nm, about 25 nm, about 30 nm, about 35 nm, about 40 nm, about 45 nm, about 50 nm, about 55 nm, about 60 nm, about 65 nm, about 70 nm, about 75 nm, about 80 nm, about 85 nm, about 90 nm, about 95 nm, about 100 nm, or any range or value therein. The hybrid nanodot may have a particle size of about 2 to 50 nm, or about 2 nm, about 4 nm, about 6 nm, about 8 nm, about 10 nm, about 12 nm, about 14 nm, about 16 nm, about 18 nm, about 20 nm, about 22 nm, about 24 nm, about 26 nm, about 28 nm, about 30 nm, about 32 nm, about 34 nm, about 36 nm, about 38 nm, about 40 nm, about 42 nm, about 44 nm, about 46 nm, about 48 nm, about 50 nm, or any value or range therein. The hybrid nanodot may have a particle size of about 5 to 40 nm, or about 5 nm, about 10 nm, about 25 nm, about 30 nm, about 35 nm, about 40 nm, about 45 nm, about 50 nm, or any value or range therein. The hybrid nanodot may have a particle size of about 7 to 20 nm, or about 8 nm, about 9 nm, about 10 nm, about 11 nm, about 12 nm, about 13 nm, about 14 nm, about 15 nm, about 16 nm, about 17 nm, about 18 nm, about 19 nm, about 20 nm, or any value or range therein.

The hybrid nanodot may exhibit excitation-dependent fluorescence emission. The excitation-dependent fluorescence emission may be of high quantum yield. This advantageously may allow for simultaneous staining of bacteria.

The hybrid nanodot may be used for fluorescence-based imaging of cells, preferably bacteria. The bacteria may be gram negative or gram positive.

The hybrid nanodot may substantially consist of a hydrophobic sp2 carbon network with hydrophilic functional groups on the surface. Non-limiting examples of such hydrophilic functional groups include hydroxyl, carbonyl, carboxyl, amino, sulfhydryl and phosphate. The hydrophilic functional groups may be used for conjugation with biomolecules such as aptamers or antibodies.

The present disclosure also relates to a process for producing a hybrid nanoparticle, comprising the process steps of:

(a) dissolving the amino acid and polycationic polymer in an aqueous medium;
(b) heating the obtained solution at elevated temperature and increased pressure; and
(c) separating the hybrid nanoparticles that have formed from the reaction mixture.

The hybrid nanoparticle produced in the above process may be a hybrid nanodot as disclosed herein. The hybrid nanodot may be made by a process comprising a step of reacting a mixture of an amino acid and a polymer selected from polycationic polymers or any copolymers or derivatives of these polymers under hydrothermal reaction conditions.

The aqueous medium used in the above reaction may be water.

The temperature of step (b) may be between about 120 to 250° C., about 120 to 240° C., about 120 to 230° C., about 120 to 220° C., about 120 to 210° C., about 120 to 200° C., about 120 to 190° C., about 120 to 180° C., about 120 to 170° C., about 120 to 160° C., about 120 to 150° C., about 120 to 140° C., about 120 to 130° C., about 130 to 250° C., about 140 to 250° C., about 150 to 250° C., about 160 to 250° C., about 170 to 250° C., about 180 to 250° C., about 190 to 250° C., about 200 to 250° C., about 210 to 250° C., about 220 to 250° C., about 230 to 250° C., about 240 to 250° C., or about 120° C., about 130° C., about 140° C., about 150° C., about 160° C., about 170° C., about 180° C., about 190° C., about 200° C., about 210° C., about 220° C., about 230° C., about 240° C., about 250° C., or any range or value therein. The temperature of step (b) may be between about 150 to 210° C., or about 150° C., about 155° C., about 160° C., about 165° C., about 170° C., about 175° C., about 180° C., about 185° C., about 190° C., about 195° C., about 200° C., about 205° C., about 210° C., or any value or range therein. The temperature of step (b) may be between about 170 to 190° C., or about 170° C., about 172° C., about 174° C., about 176° C., about 178° C., about 180° C., about 182° C., about 184° C., about 185° C., or any value or range therein.

The increased pressure in step (b) may be achieved by hydrothermal reaction in an autoclave.

The reaction in step (b) may be run for about 1 to 48 hours, about 1 to 46 hours, about 1 to 44 hours, about 1 to 42 hours, about 1 to 40 hours, about 1 to 38 hours, about 1 to 36 hours, about 1 to 34 hours, about 1 to 32 hours, about 1 to 30 hours, about 1 to 28 hours, about 1 to 26 hours, about 1 to 24 hours, about 1 to 22 hours, about 1 to 20 hours, about 1 to 18 hours, about 1 to 16 hours, about 1 to 14 hours, about 1 to 12 hours, about 1 to 10 hours, about 1 to 8 hours, about 1 to 6 hours, about 1 to 4 hours, about 1 to 2 hours, about 2 to 48 hours, about 4 to 48 hours, about 6 to 48 hours, about 8 to 48 hours, about 10 to 48 hours, about 12 to 48 hours, about 14 to 48 hours, about 16 to 48 hours, about 18 to 48 hours, about 20 to 48 hours, about 22 to 48 hours, about 24 to 48 hours, about 26 to 48 hours, about 28 to 48 hours, about 30 to 48 hours, about 32 to 48 hours, about 34 to 48 hours, about 36 to 48 hours, about 38 to 48 hours, about 40 to 48 hours, about 42 to 48 hours, about 44 to 48 hours, about 46 to 48 hours, or about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hour, about 22 hours, about 23 hours, about 24 hours, about 25 hours, about 26 hours, about 27 hours, about 28 hours, about 29 hours, about 30 hours, about 31 hour, about 32 hours, about 33 hours, about 34 hours, about 35 hours, about 36 hours, about 37 hours, about 38 hours, about 39 hours, about 40 hours, about 41 hour, about 42 hours, about 43 hours, about 44 hours, about 45 hours, about 46 hours, about 47 hours, about 48 hours, or any range or value therein. The reaction in step (b) may be run for about 2 to 36 hours, or about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hour, about 22 hours, about 23 hours, about 24 hours, about 25 hours, about 26 hours, about 27 hours, about 28 hours, about 29 hours, about 30 hours, about 31 hour, about 32 hours, about 33 hours, about 34 hours, about 35 hours, about 36 hours, or any value or range therein. The reaction in step (b) may be run for about 20 to 30 hours, or about 20 hours, about 21 hour, about 22 hours, about 23 hours, about 24 hours, about 25 hours, about 26 hours, about 27 hours, about 28 hours, about 29 hours, about 30 hours, or any value or range therein. The reaction in step (b) may be run for about 23 to 25 hours, or about 23 hours, about 24 hours, about 25 hours, or any value or range therein.

The produced hybrid nanodots may be separated from the reaction mixture by a suitable separation technique known in the art. Non-limiting examples of such separation technique include centrifugation to remove precipitate, filtration to remove precipitate, dialysis with a given weight cut off against purified water, preferably a weight cut off of about 3,000 g/mol, and lyophilizing and re-suspending the obtained product in ultrapure water. The separation technique used in the above reaction may be one, several or all of the above options.

The separation step (c) may comprise one, several or all of the following steps:
    (a) centrifugation to remove precipitate;
    (b) filtration to remove precipitate;
    (c) dialysis with a given weight cut off against purified water; and
    (d) lyophilizing and re-suspending the obtained product in ultrapure water.

In the above step (cc), the weight cut off may be in the range of about 1000 g/mol to about 5000 g/mol. The weight cut off may be in the range of about 1000 g/mol to about 5000 g/mol, about 1200 g/mol to about 5000 g/mol, about 1400 g/mol to about 5000 g/mol, about 1600 g/mol to about 5000 g/mol, about 1800 g/mol to about 5000 g/mol, about 2000 g/mol to about 5000 g/mol, about 2200 g/mol to about 5000 g/mol, about 2400 g/mol to about 5000 g/mol, about 2600 g/mol to about 5000 g/mol, about 2800 g/mol to about 5000 g/mol, about 3000 g/mol to about 5000 g/mol, about 3200 g/mol to about 5000 g/mol, about 3400 g/mol to about 5000 g/mol, about 3600 g/mol to about 5000 g/mol, about 3800 g/mol to about 5000 g/mol, about 4000 g/mol to about 5000 g/mol, about 4200 g/mol to about 5000 g/mol, about 4400 g/mol to about 5000 g/mol, about 4600 g/mol to about 5000 g/mol, about 4800 g/mol to about 5000 g/mol, about 1000 g/mol to about 4800 g/mol, about 1000 g/mol to about 4600 g/mol, about 1000 g/mol to about 4400 g/mol, about 1000 g/mol to about 4200 g/mol, about 1000 g/mol to about 4000 g/mol, about 1000 g/mol to about 3800 g/mol, about 1000 g/mol to about 3600 g/mol, about 1000 g/mol to about 3400 g/mol, about 1000 g/mol to about 3200 g/mol, about 1000 g/mol to about 3000 g/mol, about 1000 g/mol to about 2800 g/mol, about 1000 g/mol to about 2600 g/mol, about 1000 g/mol to about 2400 g/mol, about 1000 g/mol to about 2200 g/mol, about 1000 g/mol to about 2000 g/mol, about 1000 g/mol to about 1800 g/mol, about 1000 g/mol to about 1600 g/mol, about 1000 g/mol to about 1400 g/mol, about 1000 g/mol to about 1200 g/mol, or about 1000 g/mol, about 1200 g/mol, about 1400 g/mol, about 1600 g/mol, about 1800 g/mol, about 2000 g/mol, about 2200 g/mol, about 2400 g/mol, about 2600 g/mol, about 2800 g/mol, about 3000 g/mol, about 3200 g/mol, about 3400 g/mol, about 3600 g/mol, about 3800 g/mol, about 4000 g/mol, about 4200 g/mol, about 4400 g/mol, about 4600 g/mol, about 4800 g/mol, about 5000 g/mol, or any value or range therein. In one embodiment, the weight cut off is about 3000 g/mol.

The hybrid nanodot may be for combating bacteria. The bacteria may be gram negative, gram positive or multidrug-resistant. Non-limiting examples of bacteria include *E. coli*, *S. aureus* and *P. Aeruginosa*.

The present disclosure also relates to an antimicrobial composition comprising a hybrid nanodot as disclosed herein, optionally together with customary solvents, additives or fillers. Such solvents may be aqueous or organic solvents known in the art such as water, ethanol, isopropyl alcohol or mixtures thereof. The solvent may be ultrapure water.

In the antimicrobial composition, the hybrid nanodot may be dispersed in an aqueous medium at a concentration of at least about 50 μg/mL, preferably of about 100 μg/mL to 10 mg/L, more preferably 150 μg/mL to 1 mg/L. The concentration may be in the range of about 50 μg/mL to about 10,000 μg/mL, about 100 μg/mL to about 10,000 μg/mL, about 200 μg/mL to about 10,000 μg/mL, about 300 μg/mL to about 10,000 μg/mL, about 400 μg/mL to about 10,000 μg/mL, about 500 μg/mL to about 10,000 μg/mL, about 600 μg/mL to about 10,000 μg/mL, about 700 μg/mL to about 10,000 μg/mL, about 800 μg/mL to about 10,000 μg/mL, about 900 μg/mL to about 10,000 μg/mL, about 50 μg/mL to about 900 μg/mL, about 50 μg/mL to about 850 μg/mL, about 50 μg/mL to about 800 μg/mL, about 50 μg/mL to about 750 μg/mL, about 50 μg/mL to about 700 μg/mL, about 50 μg/mL to about 650 μg/mL, about 50 μg/mL to about 600 μg/mL, about 50 μg/mL to about 550 μg/mL, about 50 μg/mL to about 500 μg/mL, about 50 μg/mL to about 450 μg/mL, about 50 μg/mL to about 400 μg/mL, about 50 μg/mL to about 350 μg/mL, about 50 μg/mL to about 300 μg/mL, about 50 μg/mL to about 200 μg/mL, about 50 μg/mL to about 100 μg/mL, or about 50 μg/mL, about 100 μg/mL, about 200 μg/mL, about 300 μg/mL, about 400 μg/mL, about 500 μg/mL, about 600 μg/mL, about 700 μg/mL, about 800 μg/mL, about 900 μg/mL, about 10,000 μg/mL, or any value or range therein.

The present disclosure also relates to the use of the disclosed antimicrobial compositions to combat gram-positive and/or gram-negative bacteria in hygiene applications, preferably surface disinfection.

The hybrid nanodot may be employed in a method of combating bacteria by exposing the bacteria to the hybrid nanodot.

BRIEF DESCRIPTION OF DRAWINGS

The accompanying drawings illustrate a disclosed embodiment and serves to explain the principles of the disclosed embodiment. It is to be understood, however, that the drawings are designed for purposes of illustration only, and not as a definition of the limits of the invention.

FIG. 1A shows the absorbance and photoluminescence spectra of SPdots. FIG. 1B is a graph showing the enhanced photostability of SPdots as compared to polyethylenimine-dot (PEI-dot) and serine dot (Ser-dot) respectively.

FIG. 3A shows the transmission electron micrograph of SPdots and the inset shows the selected area electron diffraction (SAED) pattern of SPdots. FIG. 3B is a comparative graph showing the Zeta potential of SPdots of the present invention versus polyethylenimine (PEI), polyethylenimine-dot (PEI-dot), and serine dot (Ser-dot). FIG. 3C is a comparative graph showing the Zeta potentials of SPdots synthesized at varied concentration ratio of serine to polyethylenimine (PEI) (0.5:1 (S0.5P1), 1:1 (S1P1), 2:1 (S2P1) and 4:1 (S4P1)). FIG. 3D shows the MTT assay results of SPdots.

FIGS. 4A, 4B, 4C and 4D show the characterization of the surface functional groups present in SPdots by X-ray Photoelectron Spectroscopy (XPS). FIG. 4A shows the XPS survey scan of SPdots. FIG. 4B shows the C1s detailed scan for SPdots. FIG. 4C shows the N1s detailed scan for SPdots. FIG. 4D shows the O1s detailed scan for SPdots.

FIG. 5A is a graph showing the minimum inhibitory concentration (MIC) of SPdots. FIG. 5B is a graph showing the inhibition rate of SPdots against *E. coli* and *S. aureus*.

FIGS. 6A and 6B show the results of a time-kill kinetic assay of SPdots. FIG. 6A is a graph showing the time-kill kinetic assay of SPdots against *E. coli* and the inset shows the image of colonies formed on Tryptic Agar Plate by SPdots treated *E. coli* after 40 minutes of incubation. FIG. 6B is a graph showing the time-kill kinetic assay of SPdots against *S. aureus* and the inset shows the image of colonies formed on Tryptic Agar Plate by SPdots treated *S. aureus* after 60 minutes of incubation.

FIGS. 8A, 8B, 8C and 8D shows the inhibition of bacteria growth study for various antimicrobial agents, including (1) SPdots synthesized from PEI of varying molecular weights (SP800, SP1800 and SP25000), (2) Ser-dot, and (3) penicillin/streptomycin (PS control). FIG. 8A is a graph showing the minimum inhibitory concentration (MIC) values of various antimicrobial agents against *E. coli* after 24 hours of treatment. FIG. 8B is a graph showing the MIC values of various antimicrobial agents against *S. aureus* after 24 hours of treatment. FIG. 8C is a series of photographs showing bactericidal effect of (1) various SPdots, (2) Ser-dot, and (3) PS control against *E. coli* after 24 hours of treatment. FIG. 8D is a series of photographs showing bactericidal effect of (1) various SPdots, (2) Ser-dot, and (3) PS control against *S. aureus* after 24 hours of treatment.

FIG. 9A shows the fluorometric assessment of *E. coli* membrane permeabilization by SPdots using 3,3'-Dipropylthiadicarbocyanine iodide (DiSC3(5)). FIG. 9B shows the fluorometric assessment of *S. aureus* membrane permeabilization by SPdots using DiSC3(5). FIG. 9C shows the confocal laser scanning microscopy (CLSM) images of fluorescently stained live *E. coli* and SPdots treated E. coli. FIG. 9D shows the SDS-PAGE images of E. coli and S. aureus with and without treatment of SPdots.

FIG. 10 is a general schematic illustrating the possible antimicrobial mechanism of SPdots.

EXAMPLES

Non-limiting examples of the invention and a comparative example will be further described in greater detail by reference to specific Examples, which should not be construed as in any way limiting the scope of the invention.

Example 1: Antimicrobial Nanodots Synthesis

The antimicrobial nanodots were synthesized via a one-step hydrothermal process as depicted in Scheme 1. This process enables a rapid, cost-efficient and environmental friendly route to prepare the nanodots as it eliminates the usage of toxic chemical and sophisticated synthetic process.

Briefly, an amino acid (e.g. 0.72 g of serine) and a polymeric precursor (e.g., 0.36 g of branched PEI with average molecular weight ~2,000 by Light Scattering) were mixed in 36 mL of $H_2O$ at this optimized weight ratio and stirred until they dissolve completely. The resultant precursor mixture was then transferred into a stainless steel autoclave and heated at 180° C. for 24 hours. After naturally cooling down to room temperature, the as-obtained product was centrifuged at 10,000 rpm for 60 minutes, followed by filtration through 0.22 μm syringe filter to remove any precipitate. Subsequently, the product was dialyzed using a dialysis bag (Molecular Weight Cut-off=3000 Da) against ultrapure water for two days. The product was lyophilized and then resuspended in ultrapure water to obtain a reddish-brown suspension of Serine-PEI dots (SPdots). After thorough characterization, the SPdots were found to possess many unique physiochemical properties, including superior photoluminescence, small size, neutral charge, and abundant surface functional groups, which are highly useful in bacteria detection and antibacterial application.

Scheme 1. Synthesis of antimicrobial fluorescent SPdots from the biomolecule and polymer precursors.

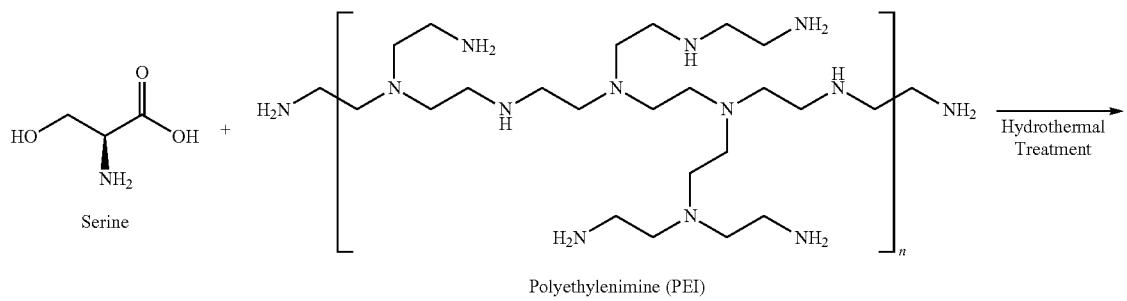

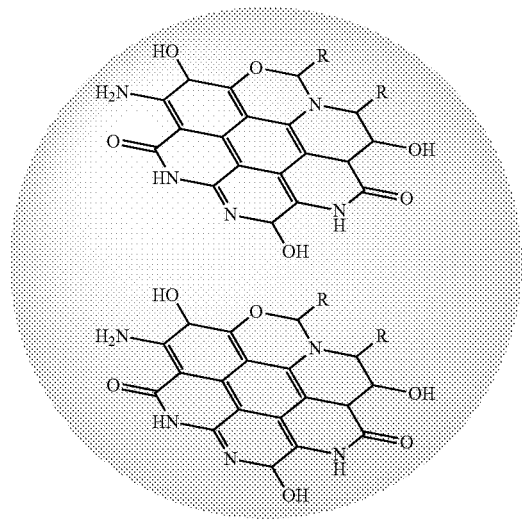

Photoluminescent Amphiphilic SP dots

Example 2: Superior Photoluminescence Properties for Sensing Applications

Figure 1A:
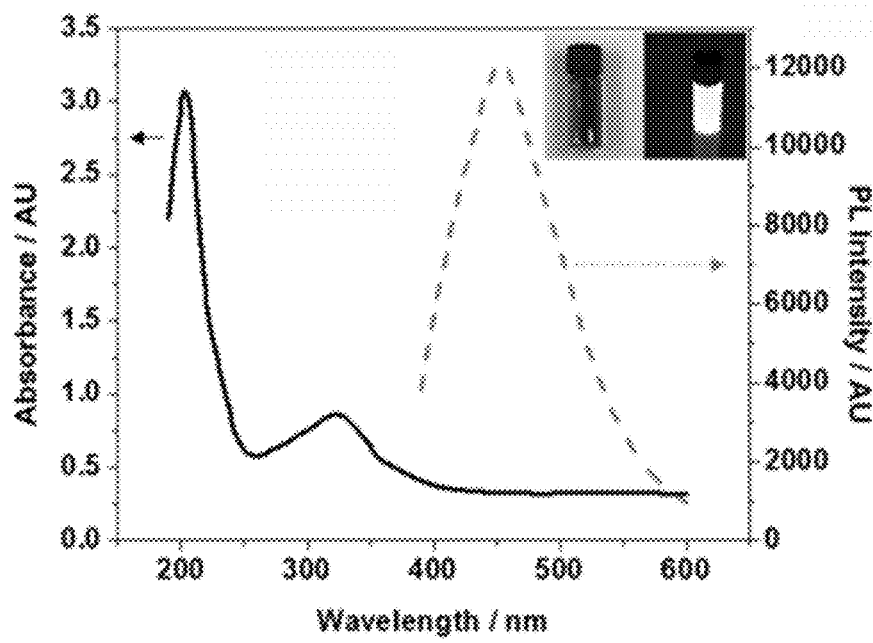
FIGS. 1A and 1B show the characterization of the optical properties of Serine-Polyethylenimine dots (SPdots) of the present invention.
Figure 1B:
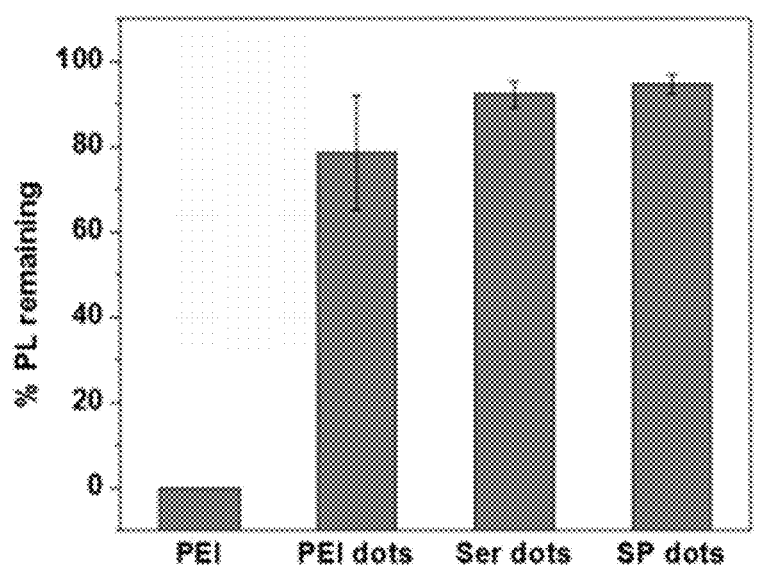

A series of measurement were carried out to characterize the optical properties of SPdots. As shown in FIG. 1A, the UV-vis absorption spectrum of nanodots exhibits two peaks centered at 200 nm and 320 nm, which could be ascribed to π-π* and n-π* transitions, respectively. Upon UV irradiation at 365 nm, the nanodots exhibited bright cyanine fluorescence (Inset of FIG. 1A). The SP dot displayed an excitation-dependent wavelength. When the excitation wavelength was tuned from 330 nm to 600 nm, the emission peaks of nanodots were also red-shifted, where a maximum emission was achieved at 450 nm at 350 nm excitation wavelength (FIG. 1A). Such excitation dependent emission property could potentially enable the nanodots to be used as an efficient fluorescent tracker in multicolor imaging. In addition, it was observed that the photostability of the SPdots is the highest amongst PEI, PEI-derived dots (PEI-dots) and serine derived dots (Ser-dot), with close to 100% of PL intensity being conserved after 30 minutes of continuous UV irradiation (FIG. 1B). Furthermore, the quantum yield (QY) of the SPdots was measured to be 11.4% (Table 1), which is sufficiently high for sensitive bacterial detection.

TABLE 1

Quantum yield comparison of PEI, PEI-dot, Ser-dot and SPdot.

| Sample | Quantum yield % |
| --- | --- |
| PEI | 0 |
| PEI-dot | 6.7 |
| Ser-dot | 27.0 |
| SPdot | 11.4 |

Example 3: Fast Fluorescent Bacterial Staining

Figure 2:
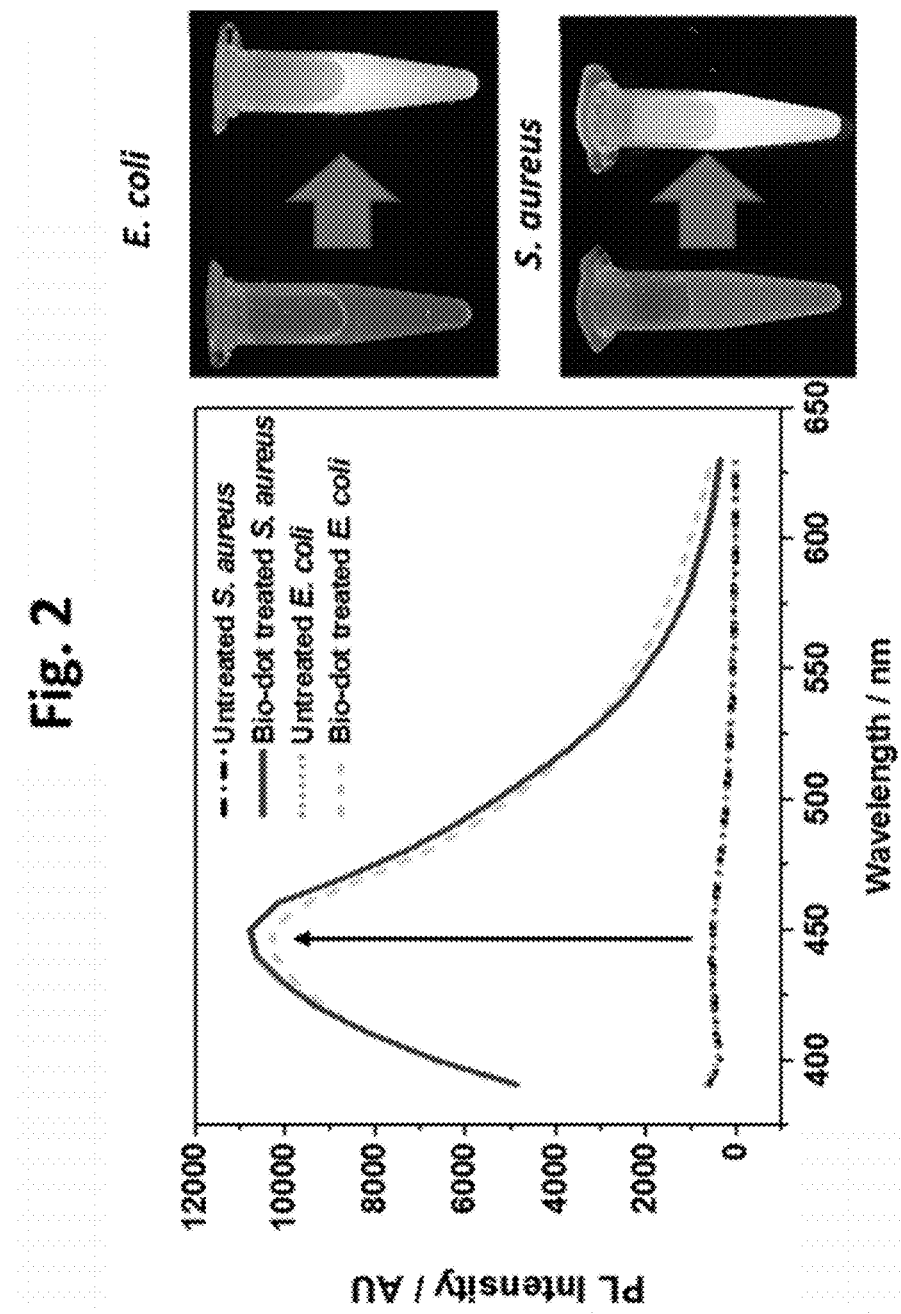
FIG. 2 shows the fluorescence spectra and images of *E. coli* and *S. aureus* before and after treatment with SPdots.

As demonstrated by Example 2, the nanodots not only exhibit an interesting excitation-dependent fluorescence, but also a sufficiently high Quantum Yield. It was also observed that the SPdots could efficiently stain/label the bacteria, allowing the bacteria to display bright fluorescence (FIG. 2). In addition, it is worthy to note that the staining process has occurred rapidly as the bacteria became fluorescent only after 5 minutes of incubation. This indicates a high potential for fast bacteria sensing application.

Figure 3A:
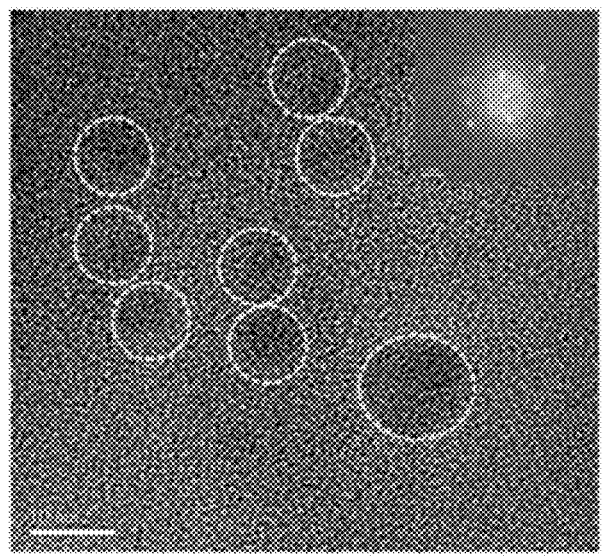
FIGS. 3A, 3B, 3C, and 3D show the characterization of the sizes, surface properties and biocompatibility of SPdots.
Figure 3B:
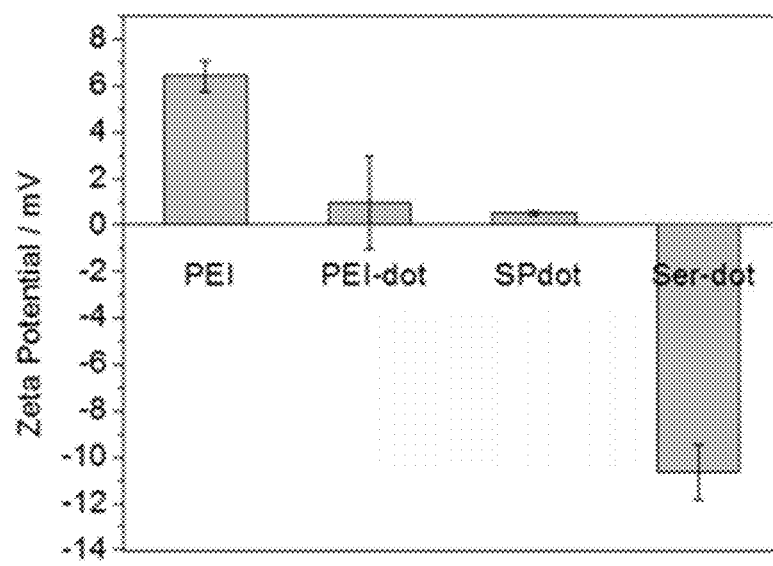
Figure 3C:
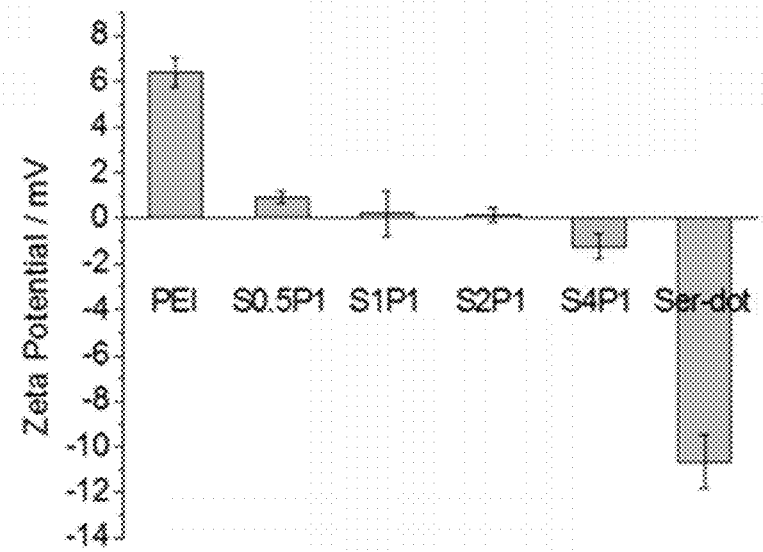
Figure 3D:
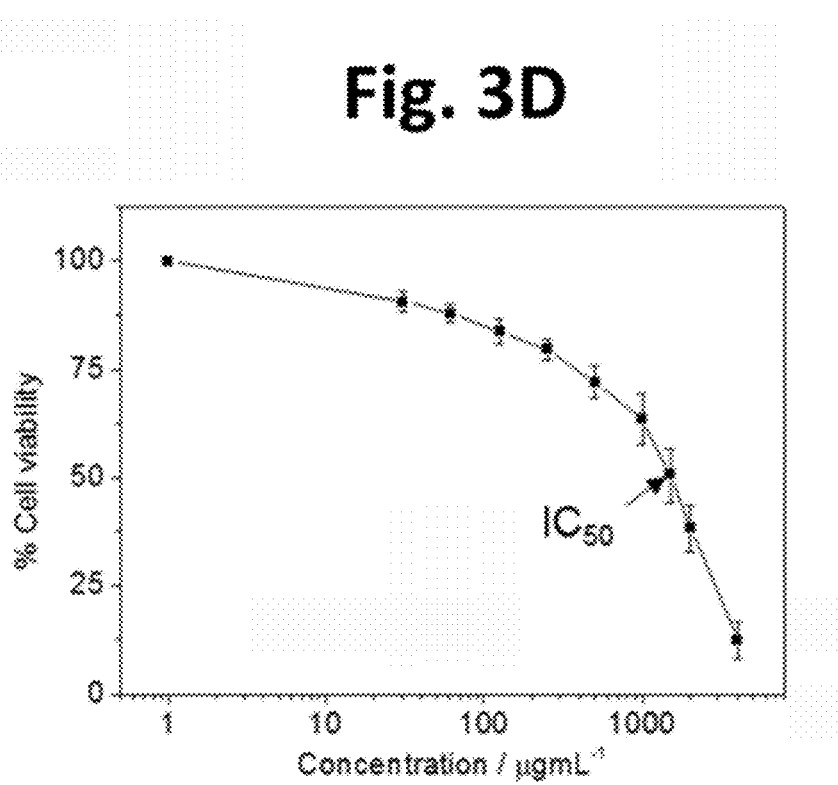

Example 4: Controlled Size and Surface Properties for Better Biocompatibility The size and surface potential of a nanodot play important roles in ensuring excellent cellular uptake and compatibility. As shown in FIG. 3A, transmission electron microscopy images reveal that SPdots exhibit an average size of ~10 nm with good dispersity and uniformity. On another note, it is known that nanodots that possess high charged surfaces tend to have high toxicity or repulsion interaction towards mammalian cells. Hence, to achieve excellent biocompatibility, the precursors for the SPdots were selected carefully. Being a highly positively charged molecule, PEI is known for its high cytotoxicity. It was found that serine can be used to balance the positive charge of PEI, thus reducing the overall charge of the nanodots (FIG. 3B), and potentially improving the biocompatibility of SPdots. Thus, by finely controlling the serine to polymer ratio of the nanodots, the surface charge/zeta potential could be fine-tuned. At the weight ratio of 2:1, the zeta potential was found to be near neutral (FIG. 3C). Unlike the conventional cationic peptide or polymer based antibacterial agent which possesses high positive charge, leading to severe cytotoxicity, the SPdots exhibit near-neutral surface charge which assures good biocompatibility. Further, the biocompatibility of SPdots was evaluated via MTT cell proliferation assay. When tested against a model mammalian cell line (HeLa cells), it was observed that SPdots can achieve a high $IC_{50}$ value of 1500 μg/mL (FIG. 3D).

Figure 4A:
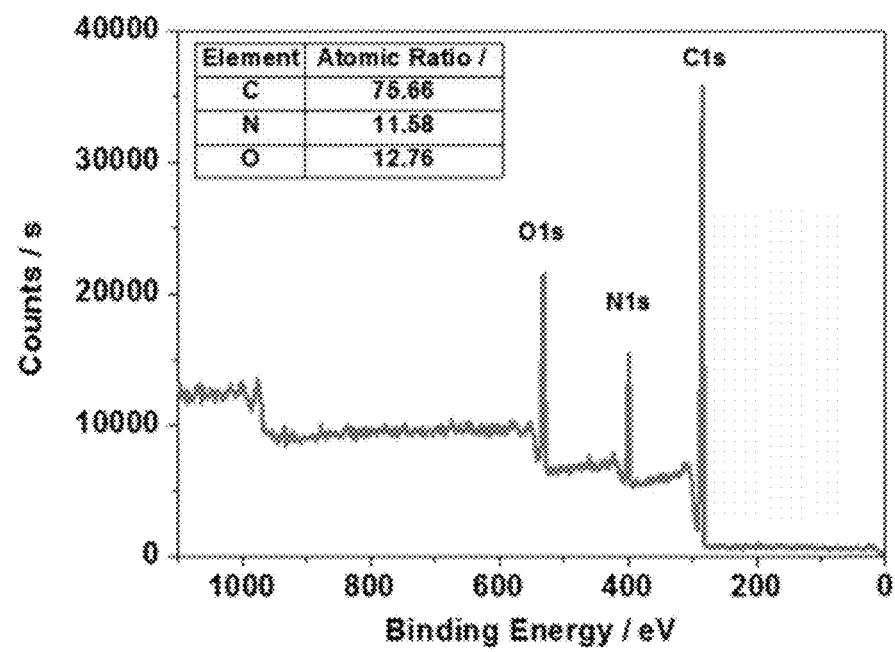
Figure 4B:
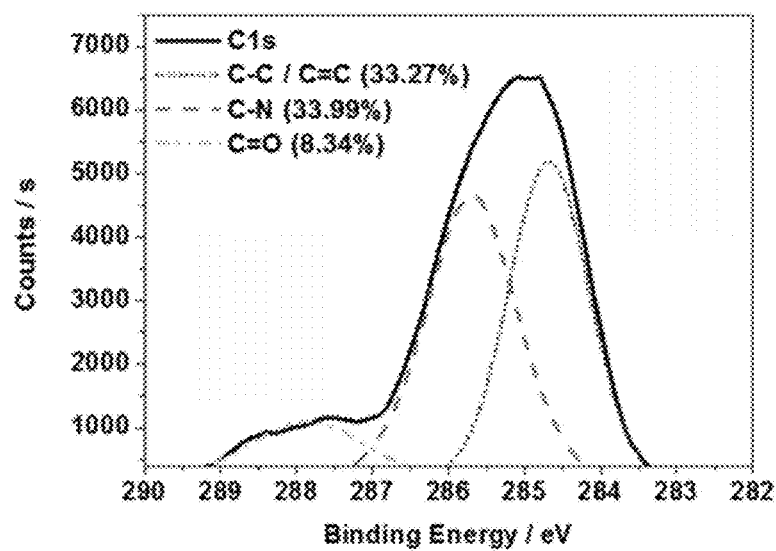

The surface functional groups present in SPdots were characterized by X-ray Photoelectron Spectroscopy (XPS). The SPdots were determined to consist of 75.66% carbon, 11.58% nitrogen and 12.76% oxygen atoms (FIG. 4A). Detailed analysis of the deconvolution signals of C1s, N1s and O1s in the nanodots shows the presence of abundant functional groups (i.e., C—C/C=C, C—N, C=O, C—O—C/C—OH, N—H, C—N—C, N—(C)3) (FIG. 4B-D). This analysis suggests that the structure of SPdots consists of a hydrophobic $sp^2$ carbon network surrounded with hydrophilic functional groups on the surface. Since the lipid bilayers of bacterial membrane consist of a hydrophilic head connected to a hydrophobic tail, the amphipathic nature of SPdots is expected be highly suitable for cell membrane interaction. In addition, the rich chemical functionalities of SPdots would allow facile conjugation with aptamers or antibodies for selective detection of a particular bacteria of interest.

Example 5: Effective Immediate Inhibition of Bacteria Growth

Figure 5A:
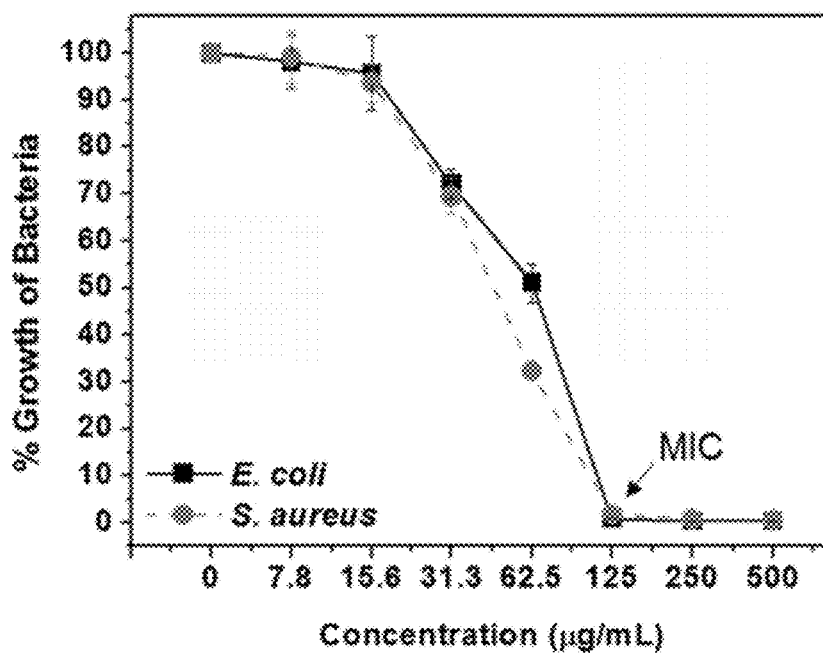
FIGS. 5A and 5B show the inhibition of bacteria growth study for SPdots.
Figure 5B:
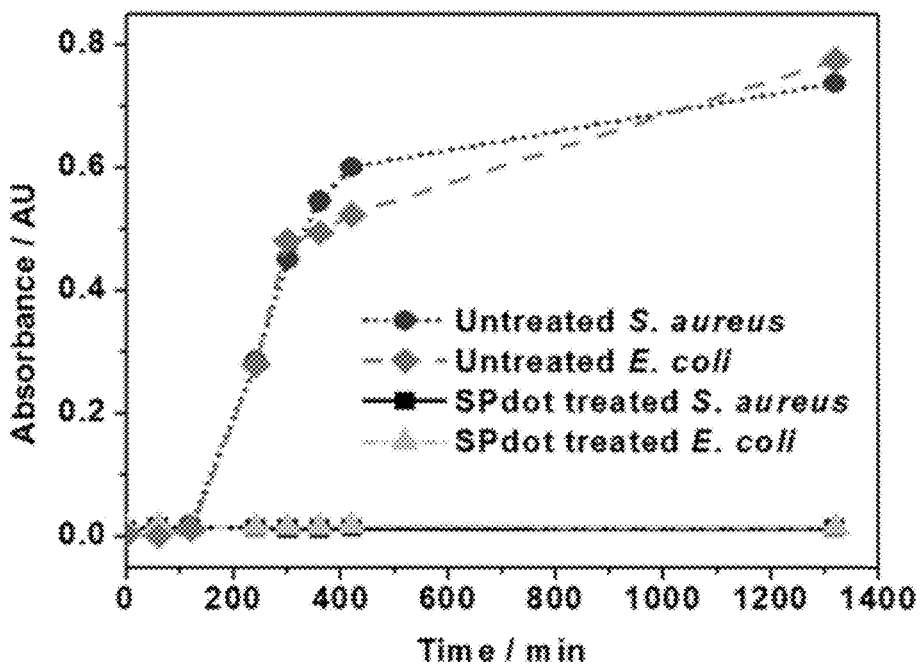

By taking advantage of the small size and near neutral surface charge, the antibacterial properties of SPdots were subsequently evaluated. The inhibition of bacteria growth was conducted via broth microdilution method. The minimum inhibitory concentration (MIC) is defined as the lowest concentration required to inhibit the growth of bacteria (>90%) after 24 hours of incubation by measuring the absorbance at 600 nm. As shown in FIG. 5A, the MIC of SPdots was determined to be 125 μg/mL, at which it can effectively inhibit (>99%) the growth of both gram-positive (*S. aureus*) and gram-negative bacteria (*E. coli*). In order to determine the time required for complete inhibition, the absorbance of the samples at 600 nm was recorded at specific time intervals during the 24 hours of incubation. As shown in FIG. 5B, the SPdots were able to achieve an immediate growth inhibition to both *E. coli* and *S. aureus* upon mixing, and the inhibition was also well sustained with no increase in bacteria population after 24 hours of monitoring.

Example 6: Fast Killing of Both Gram-Positive and Gram-Negative Bacteria

It is imperative that any antibacterial agents developed must possess a fast bactericidal rate to counter the rapid proliferation rate of the bacteria. Therefore, the time-kill kinetic study of SPdots was performed to determine the effective time for kill. As shown in FIG. 6A-B, SPdots (1×MIC) were able to eradicate more than 99% of *E. coli* and *S. aureus* at 40 minutes and 60 minutes, respectively. Such rapid elimination of bacteria would potentially limit the secretion and circulation of bacterial endo- and exotoxins, preventing septic shock and other complications. Unlike conventional antibiotics which kills bacteria slowly over the course of many hours, SPdots could kill both gram-positive and gram-negative bacteria quickly within 60 minutes, which suggests that SPdots may be developed as a promising antibacterial treatment option.

Example 7: High Therapeutic Index

The high mammalian cell biocompatibility of SPdots could be attributed to the near neutral charge of the nanodots. Overall, a satisfactory therapeutic index of 12 was achieved for the SPdots, which is better than conventional drugs such as paracetamol, indicating its potential to be used as a therapeutic agent. This also indicates that SPdots have higher selectivity towards bacteria cells than mammalian cells. More importantly, when SPdots were compared with the precursor PEI, it was found that PEI is less effective towards gram-negative E. coli and is extremely toxic to the mammalian cells (Table 2). Similarly, PEI-dots (nanodots synthesized from hydrothermal treatment of PEI precursor) are also not effective in inhibiting the bacteria and it is also quite toxic with an $IC_{50}$ value 50 times lower than that of SPdots. The well-controlled formulation of serine to PEI ratio is the key to the potent broad-spectrum antibacterial activity and the good biocompatibility here.

TABLE 2

Therapeutic Index comparison of SPdots, PEI and PEI-dots.

|  | MIC µg mL$^{-1}$ | | $IC_{50}$ µg mL$^{-1}$ | Therapeutic Index ($IC_{50}$/MIC) | |
| --- | --- | --- | --- | --- | --- |
|  | E. coli | S. aureus |  | E. coli | S. aureus |
| SPdot | 125 | 125 | 1500 | 12 | 12 |
| PEI | 500 | 125 | 30.6 | 0.06125 | 0.245 |
| PEI-dot | 500 | 250 | 250 | 0.5 | 1 |

Example 8: Effective Against Multidrug-Resistant P. Aeruginosa

Figure 7:
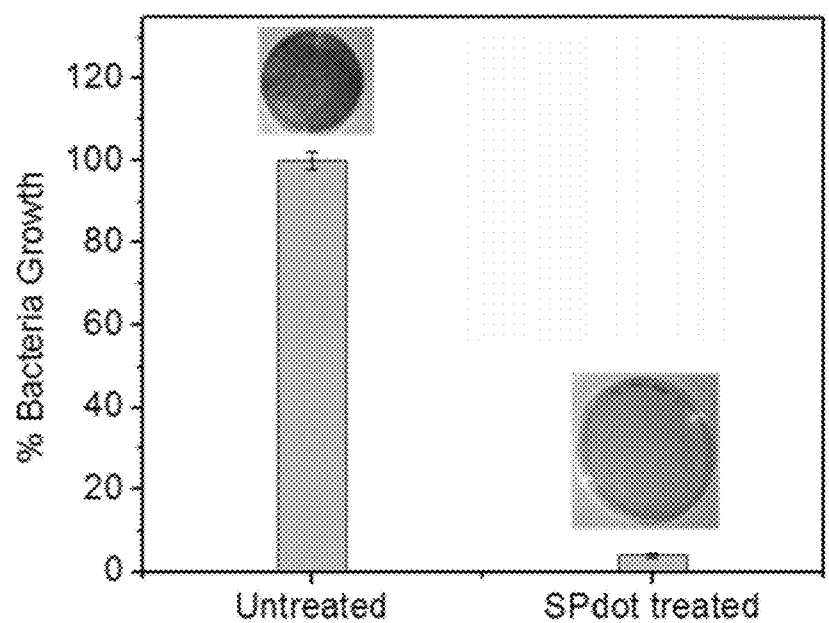
FIG. 7 is a graph showing the effective inhibition and killing of multidrug-resistant *P. Aeruginosa* by SPdots.

The development of multidrug-resistant bacteria results from the prolonged repeated exposures towards sub-lethal doses of antibiotics. The antibiotics resistance of the bacteria thrives mainly through the accumulation of resistance genes within the bacteria plasmids. In the present disclosure, it was demonstrated that the SPdots could effectively inhibit and completely kill the dangerous multidrug-resistant P. Aeruginosa (FIG. 7). It was also investigated whether the polymer precursor molecular weight length is important in controlling the antibacterial effectiveness. It was found that only SPdots with a PEI precursor molecular weight of 1800 Da is effective in killing the P. Aeruginosa whereas SPdots made from PEI of other molecular weights have been found to be less effective or even ineffective (FIG. 8A-D).

Figure 9A:
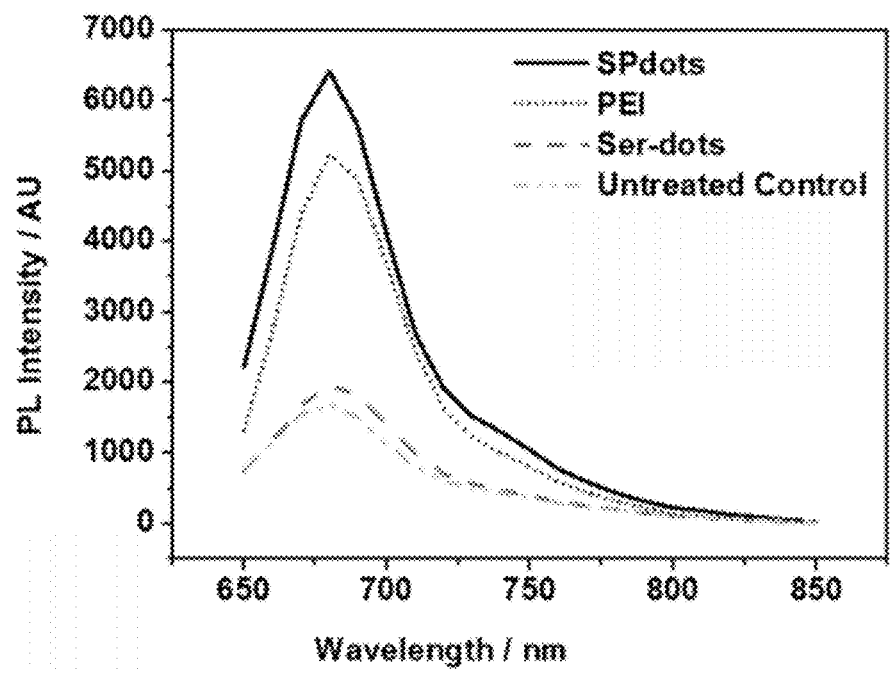
FIGS. 9A, 9B, 9C and 9D show the antibacterial mechanism evaluation of SPdots.
Figure 9B:
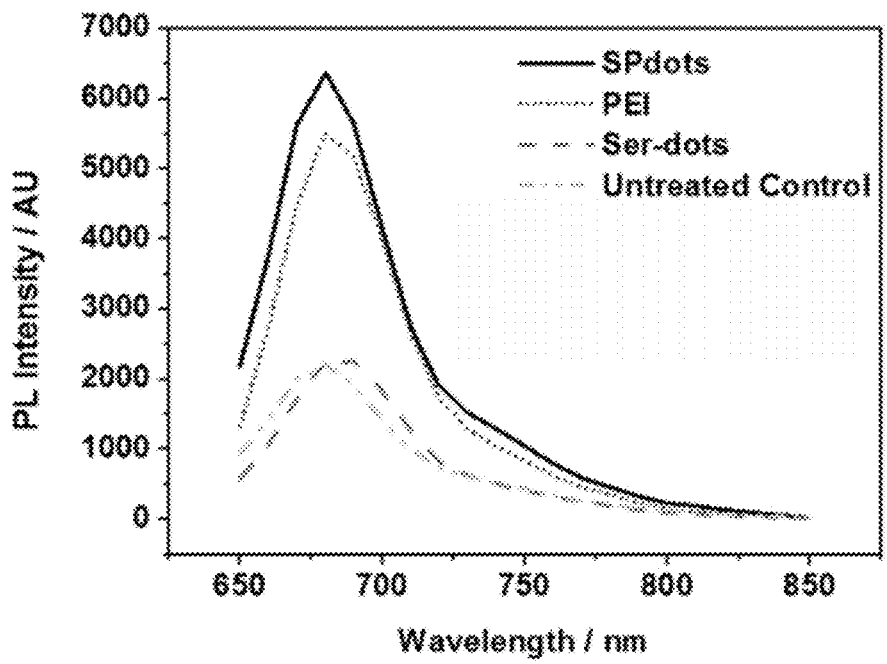
Figure 9C:
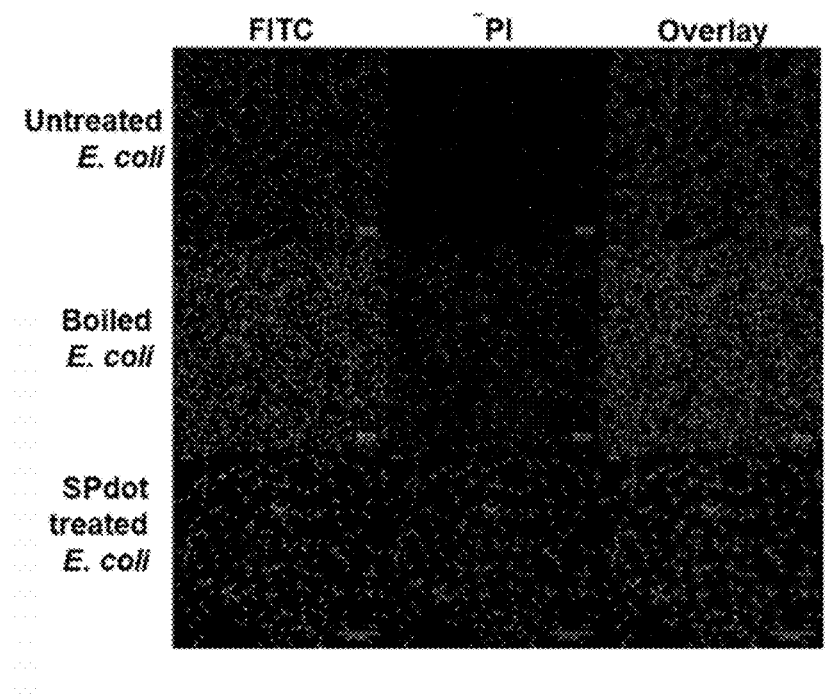
Figure 9D:
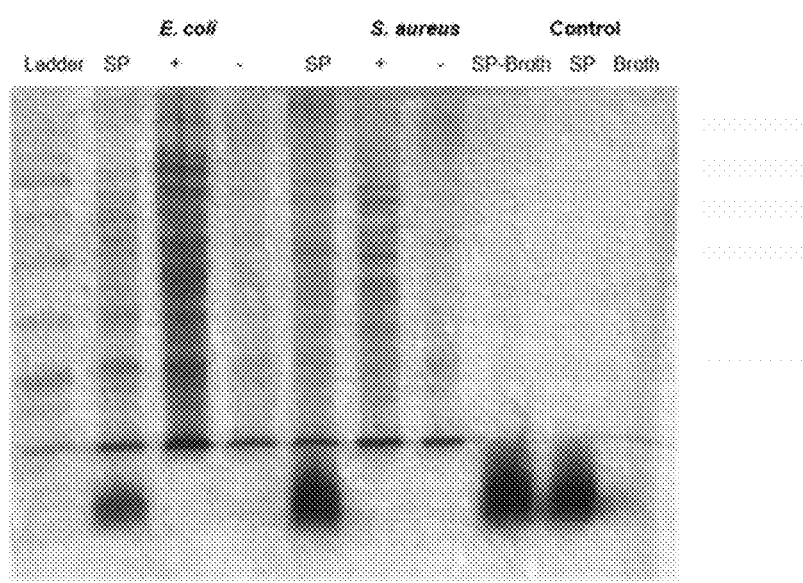

Example 9: Antibacterial Mechanism: Membrane Disruption and Intracellular Protein Release The antibacterial mechanism of SPdots was first evaluated using membrane potential assay using a cytoplasmic membrane potential sensitive dye, 3,3'-Dipropylthiadicarbocyanine iodide, DiSC3(5). DiSC3(5) typically localizes at the bacterial cytoplasmic membrane. The fluorescence is self-quenched in the normal polarized membrane, and the fluorescence is increased when the membrane is depolarized or permeabilized. Upon addition of DiSC3(5) to SPdots treated E. coli and S. aureus, an increase in fluorescence intensity could be observed while untreated bacteria showed only very weak fluorescence (FIG. 9A-B). This indicates that the membrane of the bacteria cells was depolarized by SPdots and that the bacterial membrane was permeabilized. In addition, confocal laser scanning microscopy (CLSM) was also used to observe SPdots treated bacteria. The SPdots-treated bacteria was incubated with propidium iodide (PI) dye, a red fluorescent dye that only labels cells with compromised membranes. Unlike untreated bacteria which displayed negligible red fluorescence, the SPdots treated bacteria were 100% stained by the red PI dye, indicating that the membrane of the bacteria cells has been destabilized (FIG. 9C). Since damaged cell membrane are susceptible to the leakage of cytoplasmic contents, SDS-PAGE was conducted to analyze the leakage. As shown in FIG. 9D, both SPdots treated E. coli and S. aureus showed significant protein bands which suggest the leakage of intracellular proteins from the damaged bacteria cell membrane. As such, as depicted in FIG. 10, it was postulated that the SPdots (1) were able to kill bacteria by physical cell membrane disruption (2) (bacteria remains intact without fragmentation), and lead to substantial proteins release from the bacteria (3), thus leading to bacterial cell death (4) and minimizing the likelihood of resistance development in bacteria.

INDUSTRIAL APPLICABILITY

The hybrid nanodots of the present disclosure may find a multiple number of applications in which their tunable photoluminescent, antimicrobial, biocompatibility and bacteria-staining properties are useful. The hybrid nanodots may be used as an efficient fluorescent tracker in multicolour imaging. The hybrid nanodot may also be used in rapid and sensitive detection of bacteria. For selective detection of a particular bacteria of interest, the hybrid nanodot may be conjugated with aptamers or antibodies by exploiting the chemical functionalities present. The hybrid nanodot may be particularly useful in inhibiting bacteria growth. The bacteria may be gram positive, gram negative or multidrug-resistant. The hybrid nanodot may also be useful as a therapeutic agent.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

What is claimed is:

1. A hybrid nanodot made by a process comprising an operation of reacting a mixture of poly(ethylene imine) (PEI) and an amino acid selected from the group consisting of serine, threonine, cysteine, tyrosine, asparagine, glutamine, lysine, aspartic acid, glutamic acid and mixtures thereof under hydrothermal reaction conditions, wherein the weight ratio of amino acid to PEI is about 3:1 to about 1:1, and wherein PEI has an average molecular weight of about 1200 g/mol to about 1800 g/mol determined by light scattering.

2. The hybrid nanodot of claim, wherein PEI is a branched poly(ethylene imine).

3. The hybrid nanodot of claim 1, wherein PEI has an average molecular weight of about 1800 g/mol determined by light scattering.

4. The hybrid nanodot of claim 1, wherein the weight ratio of amino acid to PEI is about 3:1, or about 2:1.

5. The hybrid nanodot of claim 1, wherein the particle size of the hybrid nanodot is about 1 to 100 nm.

6. The hybrid nanodot of claim 1, wherein the nanodots exhibit excitation-dependent fluorescence emission.

7. The hybrid nanodot according to claim 6 for fluorescence-based imaging of cells.

8. The hybrid nanodot of claim 1, which substantially consists of a hydrophobic $sp^2$ carbon network with hydrophilic functional groups on the surface.

9. The hybrid nanodot of claim 1, wherein the amino acid is selected from the group consisting of serine, threonine, and lysine.

10. The hybrid nanodot of claim 1, wherein the amino acid is selected from the group consisting of serine, threonine, and lysine.

11. The hybrid nanodot of claim 1, wherein the nanodot is antibacterial.

12. The hybrid nanodot of claim 1, wherein the the amino acid is selected from the group consisting of serine, threonine, and lysine, wherein the weight ratio of serine or threonine to PEI is about 3:1 or about 2:1.

13. The hybrid nanodot of claim 12, wherein PEI has an average molecular weight of about 1800 g/mol determined by light scattering.

14. A process for producing a hybrid nanodot, comprising:
(a) dissolving
  i) PEI having an average molecular weight of about 1200 g/mol to about 1800 g/mol determined by light scattering and
  ii) an amino acid selected from the group consisting of serine, threonine, cysteine, tyrosine, asparagine, glutamine, lysine, aspartic acid, glutamic acid, and a mixture thereof, in an aqueous medium to form a precursor mixture;
(b) heating the precursor mixture at a temperature between about 120° C. and about 250° C. and under hydrothermal reaction conditions in an autoclave to form a reaction mixture comprising the hybrid nanodot; and
(c) separating the hybrid nanodot from the reaction mixture;
wherein the weight ratio of amino acid to PEI is about 3:1 to about 1:1.

15. The process of claim 14, wherein the temperature in step (b) is between about 150° C. and about 210° C. or between about 170° C. and about 190° C.

16. The process of claim 14, wherein step (b) is performed from 1 to 48 hours, from 2 to 36 hours, from 20 to 30 hours, or from 23 to 25 hours.

17. A method of combating bacteria comprising exposing the bacteria to a hybrid nanodot, wherein the hybrid nanodot is made by a process comprising an operation of reacting a mixture of PEI and an amino acid selected from the group consisting of serine, threonine, cysteine, tyrosine, asparagine, glutamine, lysine, aspartic acid, glutamic acid, and mixtures thereof under hydrothermal reaction conditions, wherein the weight ratio of amino acid to PEI has an average molecular weight of about 1200 g/mol to about 1800 g/mol determined by light scattering.

* * * * *